US006168936B1

(12) United States Patent
Wang

(10) Patent No.: US 6,168,936 B1
(45) Date of Patent: Jan. 2, 2001

(54) PHENOL OXIDIZING ENZYMES

(75) Inventor: Huaming Wang, Fremont, CA (US)

(73) Assignee: Genencor International, Inc., Rochester, NY (US)

( * ) Notice: Under 35 U.S.C. 154(b), the term of this patent shall be extended for 0 days.

(21) Appl. No.: 09/401,476

(22) Filed: Sep. 22, 1999

(51) Int. Cl.$^7$ .............................. C12N 9/02; C12N 15/00; C12P 21/06; C07H 21/02

(52) U.S. Cl. ..................... 435/189; 536/23.1; 435/820.1; 435/69.1

(58) Field of Search ............................. 536/23.1; 530/300

*Primary Examiner*—Ponnathapu Achutamurthy
*Assistant Examiner*—Christian L. Fronda
(74) *Attorney, Agent, or Firm*—Genencor International, Inc.

(57) ABSTRACT

Disclosed herein are novel phenol oxidizing enzymes naturally-produced by strains of the species *Stachybotrys* which possess a pH optima in the alkaline range and which are useful in modifying the color associated with dyes and colored compounds, as well as in anti-dye transfer applications. Also disclosed herein are biologically-pure cultures of strains of the genus Stachybotrys, designated herein *Stachybotrys parvispora* MUCL 38996 and *Stachybotrys chartarum* MUCL 38898, which are capable of naturally-producing the novel phenol oxidizing enzymes.

Disclosed herein is the amino acid and nucleic acid sequence for *Stachybotrys* phenol oxidizing enzyme B as well as expression vectors and host cells comprising the nucleic acid. Disclosed herein are methods for producing the phenol oxidizing enzyme as well as methods for constructing expression hosts.

42 Claims, 8 Drawing Sheets

```
GGATCCATCA ACATGATCAG CCAAGCTATC GGAGCCGTGG CTCTGGGCCT TGCTGTGATC GGCGGCAGCT CTGTCGATGC 80
CAGATCCGTT GCTGGTCGAT CGACAGACAT GCCTTCCGGT CTCACCAAGA GGCAGACGCA GCTGAGTCCT CCCCTGGCCT 160
TGTACGAAGT GCCTCTGCCG ATCCCTCCTC TGAAGGCGCC CAAGTAGTAA GTACATTCTA TAGGCTAGCA GAGCCAACGT 240
TGCTAATCAT TGCAGTACCG TCCCCAACCC CAACACTGGA GAGGACATCT TGTACTACGA GATGGAGATT AGGCCCTTCT 320
CCCACCAGAT CTACCCTGAT CTGGAGCCGG CCAACATGGT TGGATACGAT GGCATGTCCC CAGGACCTAC CATCATCGTT 400
CCTCGTGGCA CTGAGAGTGT TGTCCGCTTC GTGAACAGCG GAGAGAACAC CTCTCCCAAC AGCGTCCACT TGCACGGCTC 480
TTTCTCTCGA GCTCCCTTTG ATGGTTGGGC TGAGGACACT ACCCAGCCTG GCGAGTACAA GGATTACTAC TACCCCAACA 560
GGCAGGCTGC CCGCATGCTT TGGTACCATG ACCATGCCAT GTCCATCACC GCCGAGAACG CCTACATGGG TCAGGCTGGT 640
GTCTACATGA TCCAGGACCC GGCTGAGGAT GCCCTGAACC TCCCCAGCGG CTACGGCGAG TTTGATATCC CCTTGGTTCT 720
GACTGCCAAG CGATACAACG CAGACGGCAC TCTCTTCTCC ACCAATGGAG AGGTTTCCAG CTTCTGGGGT GACGTTATTC 800
AAGTGGTAAG TTGAGCCCAT TGAGATGCTT CAGATCCTAG AAGTATCGAT GTATGAAATT GTGCATGCTC TAACCAGTGC 880
TATCACAGAA CGGTCAGCCT TGGCCTATGC TCAACGTGCA GCCGCGCAAG TACCGCTTCC GCTTCCTCAA CGCTGCCGTC 960
TCACGCTCTT TCGCTCTGTA TCTTGCTACC TCTGAGGATT CAGAGACCAG ACTTCCCTTC CAGGTCATTG CCGCTGACGG 1040
TGGTCTGCTT GAGGGCCCTG TTGACACTGA CACTCTGTAC ATCTCTATGG CCGAGCGCTG GGAGGTTGTT ATCGACTTCT 1120
CCACCTTCGC TGGCCAGTCC ATCGATATCC GCAACCTTCC TGGTGCTGAC GGTCTCGGTG TTGAGCCTGA GTTTGATAAC 1200
ACTGACAAGG TCATGCGATT CGTCGTTGAT GAAGTCCTTG AGTCGCCCGA CACTTCTGAG GTGCCTGCCA ACCTCCGAGA 1280
TGTTCCTTTC CCCGAGGGCG GCAACTGGGA CCCCGCAAAC CCCACTGATG ACGAGACTTT CACCTTCGGC CGTGCTAATG 1360
GACAGTGGAC AATCAACGGA GTTACCTTCT CGGATGTCGA GAACCGTCTG CTCCGCAATG TGCCCCGCGA CACTGTTGAG 1440
ATCTGGCGAC TTGAGAACAA CTCCAACGGT TGGACTCACC CTGTTCACAT TCACCTCGTT GACTTCCGAG TCCTTTCTCG 1520
TTCCACTGCC CGTGGAGTCG AGCCTTATGA GGCTGCTGGT CTCAAGGATG TTGTCTGGCT GGCTCGTCGT GAGGTTGTCT 1600
ATGTTGAGGC CCACTACGCT CCTTTCCCGT AAGTTCTCGC CTTTTACCTA ACTGGTTTTC ACTCATGCTA ACATCTACAA 1680
GTGGTGTCTA CATGTTGCAC TGCCACAACC TGATCCACGA GGACCACGAC ATGATGGCTG CTTTCAATGT CACTGTTCTC 1760
GGTGACTATG GCTACAACTA CACCGAGTTC ATTGACCCCA TGGAGCCTCT CTGGAGGCCC CGCCCCTTCC TCCTCGGAGA 1840
GTTCGAGAAT GGCTCGGGTG ACTTCAGCGA GCTTGCCATC ACTGACCGCA TTCAGGAGAT GGCTAGCTTC AACCCCTACG 1920
CCCAGGCTGA TGATGATGCC GCTGAGGAGT AGACCGGT 1958
```

FIG._1

```
MISQAIGAVA LGLAVIGGSS VDARSVAGRS TDMPSGLTKR QTQLSPPLAL YEVPLPIPPL 60
KAPNTVPNPN TGEDILYYEM EIRPFSHQIY PDLEPANMVG YDGMSPGPTI IVPRGTESVV 120
RFVNSGENTS PNSVHLHGSF SRAPFDGWAE DTTQPGEYKD YYYPNRQAAR MLWYHDHAMS 180
ITAENAYMGQ AGVYMIQDPA EDALNLPSGY GEFDIPLVLT AKRYNADGTL FSTNGEVSSF 240
WGDVIQVNGQ PWPMLNVQPR KYRFRFLNAA VSRSFALYLA TSEDSETRLP FQVIAADGGL 300
LEGPVDTDTL YISMAERWEV VIDFSTFAGQ SIDIRNLPGA DGLGVEPEFD NTDKVMRFVV 360
DEVLESPDTS EVPANLRDVP FPEGGNWDPA NPTDDETFTF GRANGQWTIN GVTFSDVENR 420
LLRNVPRDTV EIWRLENNSN GWTHPVHIHL VDFRVLSRST ARGVEPYEAA GLKDVVWLAR 480
REVVYVEAHY APFPGVYMLH CHNLIHEDHD MMAAFNVTVL GDYGYNYTEF IDPMEPLWRP 540
RPFLLGEFEN GSGDFSELAI TDRIQEMASF NPYAQADDDA AEE 583
```

FIG._2

```
CAGCTCGGTC TACTACTCTC GCTTCTCTTT GACAAATCAA ATCTACCAAT CGTTCCTTCA ATTTCAAACG ATCAACATGA 80
TCAGCCAAGC TATCGGAGCC GTGGCTCTGG GCCTTGCTGT GATCGGCGGC AGCTCTGTCG ATGCCAGATC CGTTGCTGGT 160
CGATCGACAG ACATGCCTTC CGGTCTCACC AAGAGGCAGA CGCAGCTGAG TCCTCCCCTG GCCTTGTACG AAGTGCCTCT 240
GCCGATCCCT CCTCTGAAGG CGCCCAAGTA GTAAGTACAT TCTATAGGCT AGCAGAGCCA ACGTTGCTAA TCATTGCAGT 320
ACCGTCCCCA ACCCCAACAC TGGAGAGGAC ATCTTGTACT ACGAGATGGA GATTAGGCCC TTCTCCCACC AGATCTACCC 400
TGATCTGGAG CCGGCCAACA TGGTTGGATA CGATGGCATG TCCCCAGGAC CTACCATCAT CGTTCCTCGT GGCACTGAGA 480
GTGTTGTCCG CTTCGTGAAC AGCGGAGAGA ACACCTCTCC CAACAGCGTC CACTTGCACG GCTCTTTCTC TCGAGCTCCC 560
TTTGATGGTT GGGCTGAGGA CACTACCCAG CCTGGCGAGT ACAAGGATTA CTACTACCCC AACAGGCAGG CTGCCCGCAT 640
GCTTTGGTAC CATGACCATG CCATGTCCAT CACCGCCGAG AACGCCTACA TGGGTCAGGC TGGTGTCTAC ATGATCCAGG 720
ACCCGGCTGA GGATGCCCTG AACCTCCCCA GCGGCTACGG CGAGTTTGAT ATCCCCTTGG TTCTGACTGC CAAGCGATAC 800
AACGCAGACG GCACTCTCTT CTCCACCAAT GGAGAGGTTT CCAGCTTCTG GGGTGACGTT ATTCAAGTGG TAAGTTGAGC 880
CCATTGAGAT GCTTCAGATC CTAGAAGTAT CGATGTATGA AATTGTGCAT GCTCTAACCA GTGCTATCAC AGAACGGTCA 960
GCCTTGGCCT ATGCTCAACG TGCAGCCGCG CAAGTACCGC TTCCGCTTCC TCAACGCTGC CGTCTCACGC TCTTTCGCTC 1040
TGTATCTTGC TACCTCTGAG GATTCAGAGA CCAGACTTCC CTTCCAGGTC ATTGCCGCTG ACGGTGGTCT GCTTGAGGGC 1120
CCTGTTGACA CTGACACTCT GTACATCTCT ATGGCCGAGC GCTGGGAGGT TGTTATCGAC TTCTCCACCT TCGCTGGCCA 1200
GTCCATCGAT ATCCGCAACC TTCCTGGTGC TGACGGTCTC GGTGTTGAGC CTGAGTTTGA TAACACTGAC AAGGTCATGC 1280
GATTCGTCGT TGATGAAGTC CTTGAGTCGC CCGACACTTC TGAGGTGCCT GCCAACCTCC GAGATGTTCC TTTCCCCGAG 1360
GGCGGCAACT GGGACCCCGC AAACCCCACT GATGACGAGA CTTTCACCTT CGGCCGTGCT AATGGACAGT GGACAATCAA 1440
CGGAGTTACC TTCTCGGATG TCGAGAACCG TCTGCTCCGC AATGTGCCCC GCGACACTGT TGAGATCTGG CGACTTGAGA 1520
ACAACTCCAA CGGTTGGACT CACCCTGTTC ACATTCACCT CGTTGACTTC CGAGTCCTTT CTCGTTCCAC TGCCCGTGGA 1600
GTCGAGCCTT ATGAGGCTGC TGGTCTCAAG GATGTTGTCT GGCTGGCTCG TCGTGAGGTT GTCTATGTTG AGGCCCACTA 1680
CGCTCCTTTC CCGTAAGTTC TCGCCTTTTA CCTAACTGGT TTTCACTCAT GCTAACATCT ACAAGTGGTG TCTACATGTT 1760
GCACTGCCAC AACCTGATCC ACGAGGACCA CGACATGATG GCTGCTTTCA ATGTCACTGT TCTCGGTGAC TATGGCTACA 1840
ACTACACCGA GTTCATTGAC CCCATGGAGC CTCTCTGGAG GCCCCGCCCC TTCCTCCTCG GAGAGTTCGA GAATGGCTCG 1920
GGTGACTTCA GCGAGCTTGC CATCACTGAC CGCATTCAGG AGATGGCTAG CTTCAACCCC TACGCCCAGG CTGATGATGA 2000
TGCCGCTGAG GAGTAAATAT GATGATCGTC GAATGATTTA TGGACAGCAG TATATAGCTA TTTTAGGAAA TACTTGAATA 2080
AGTTGTGGTG CTTAA                                                                         2095
```

FIG._3

```
  1 MFKHTLGAAALSL.LFNSNAVQASPVP.ETSPATGHLFKRVAQISPQYPM 48
  1 MISQAIGAVALGLAVIGGSSVDARSVAGRSTDMPSGLTKRQTQLSPPLAL 50

 49 FTVPLPIPPVKQPRLTVTNPVNGQEIWYYEVEIKPFTHQVYPDLGSADLV 98
 51 YEVPLPIPPLKAPN.TVPNPNTGEDILYYEMEIRPFSHQIYPDLEPANMV 99

 99 GYDGMSPGPTFQVPRGVETVVRFINNAE..APNSVHLHGSFSRAAFDGWA 146
100 GYDGMSPGPTIIVPRGTESVVRFVNSGENTSPNSVHLHGSFSRAPFDGWA 149

147 EDITEPGSFKDYYYPNRQSARTLWYHDHAMHITAENAYRGQAGLYMLTDP 196
150 EDTTQPGEYKDYYYPNRQAARMLWYHDHAMSITAENAYMGQAGVYMIQDP 199

197 AEDALNLPSGYGEFDIPMILTSKQYTANGNLVTTNGELNSFWGDVIHVNG 246
200 AEDALNLPSGYGEFDIPLVLTAKRYNADGTLFSTNGEVSSFWGDVIQVNG 249

247 QPWPFKNVEPRKYRFRFLDAAVSRSFGLYFADTDAIDTRLPFKVIASDSG 296
250 QPWPMLNVQPRKYRFRFLNAAVSRSFALYLATSEDSETRLPFQVIAADGG 299

297 LLEHPADTSLLYISMAERYEVVFDFSDYAGKTIELRNLGGSIGGIGTDTD 346
300 LLEGPVDTDTLYISMAERWEVVIDFSTFAGQSIDIRNLPGA.DGLGVEPE 348

347 YDNTDKVMRFVVADDTTQPDTSVVPANLRDVPFPSPTTNTP......RQF 390
349 FDNTDKVMRFVVDEVLESPDTSEVPANLRDVPFPEGGNWDPANPTDDETF 398

391 RFGRTGPTWTINGVAFADVQNRLLANVPVGTVERWELINAGNGWTHPIHI 440
399 TFGRANGQWTINGVTFSDVENRLLRNVPRDTVEIWRLENNSNGWTHPVHI 448

441 HLVDFKVISRTSGNNARTVMPYE.SGLKDVVWLGRRETVVVEAHYAPFPG 489
449 HLVDFRVLSRST...ARGVEPYEAAGLKDVVWLARREVVYVEAHYAPFPG 495

490 VYMFHCHNLIHEDHDMMAAFNATVLPDYGYNATVFVDPMEELWQARPYEL 539
496 VYMLHCHNLIHEDHDMMAAFNVTVLGDYGYNYTEFIDPMEPLWRPRPFLL 545

540 GEFQAQSGQFSVQAVTERIQTMAEYRPYAAADE 572
546 GEFENGSGDFSELAITDRIQEMASFNPYAQADD 578
```

*FIG._4*

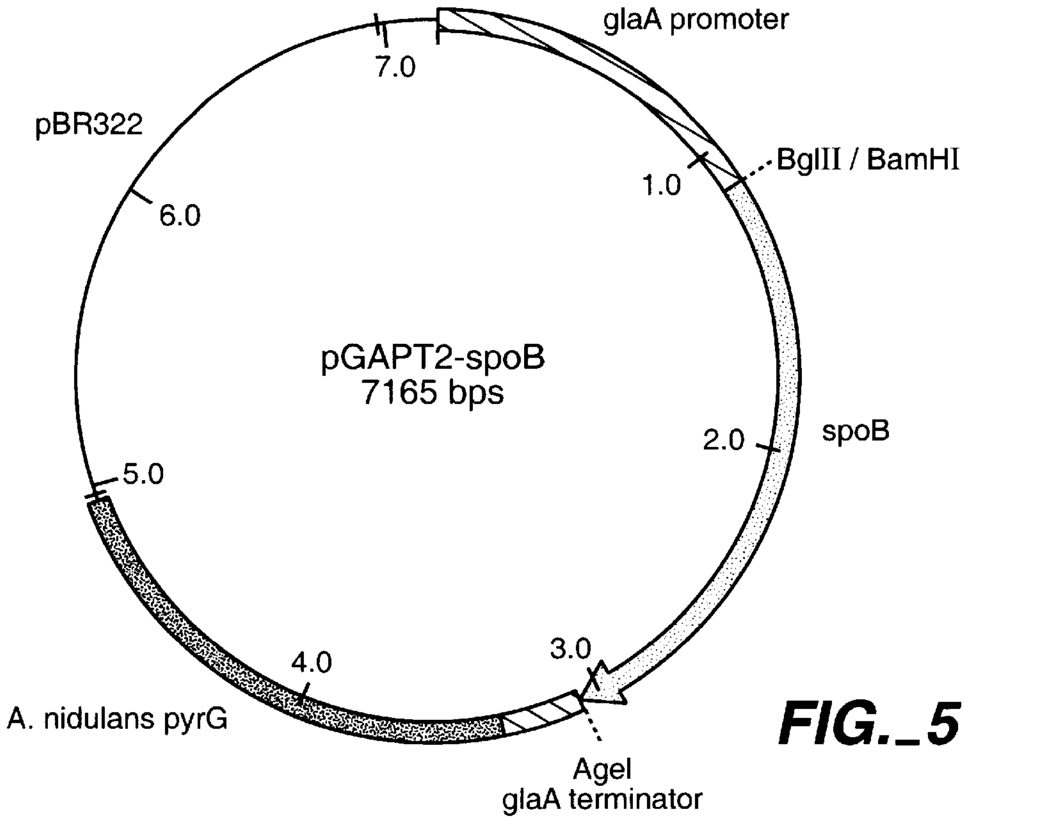
FIG._5
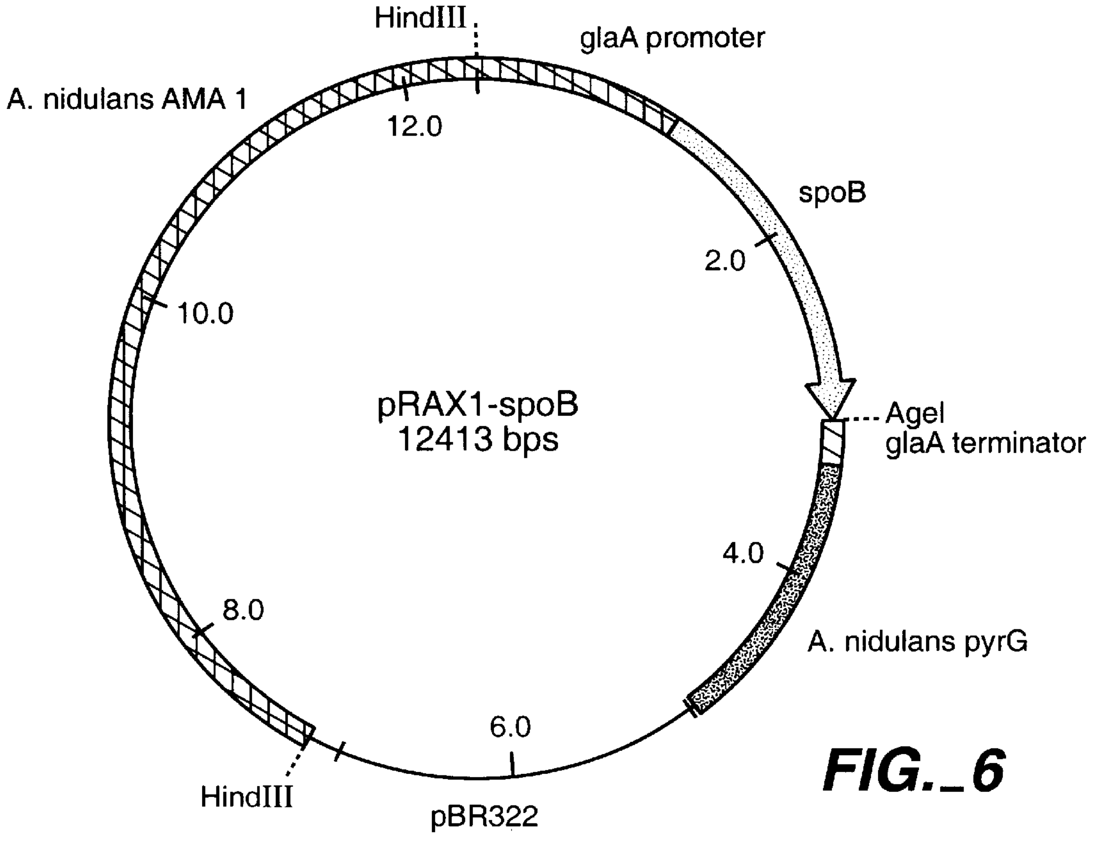
FIG._6

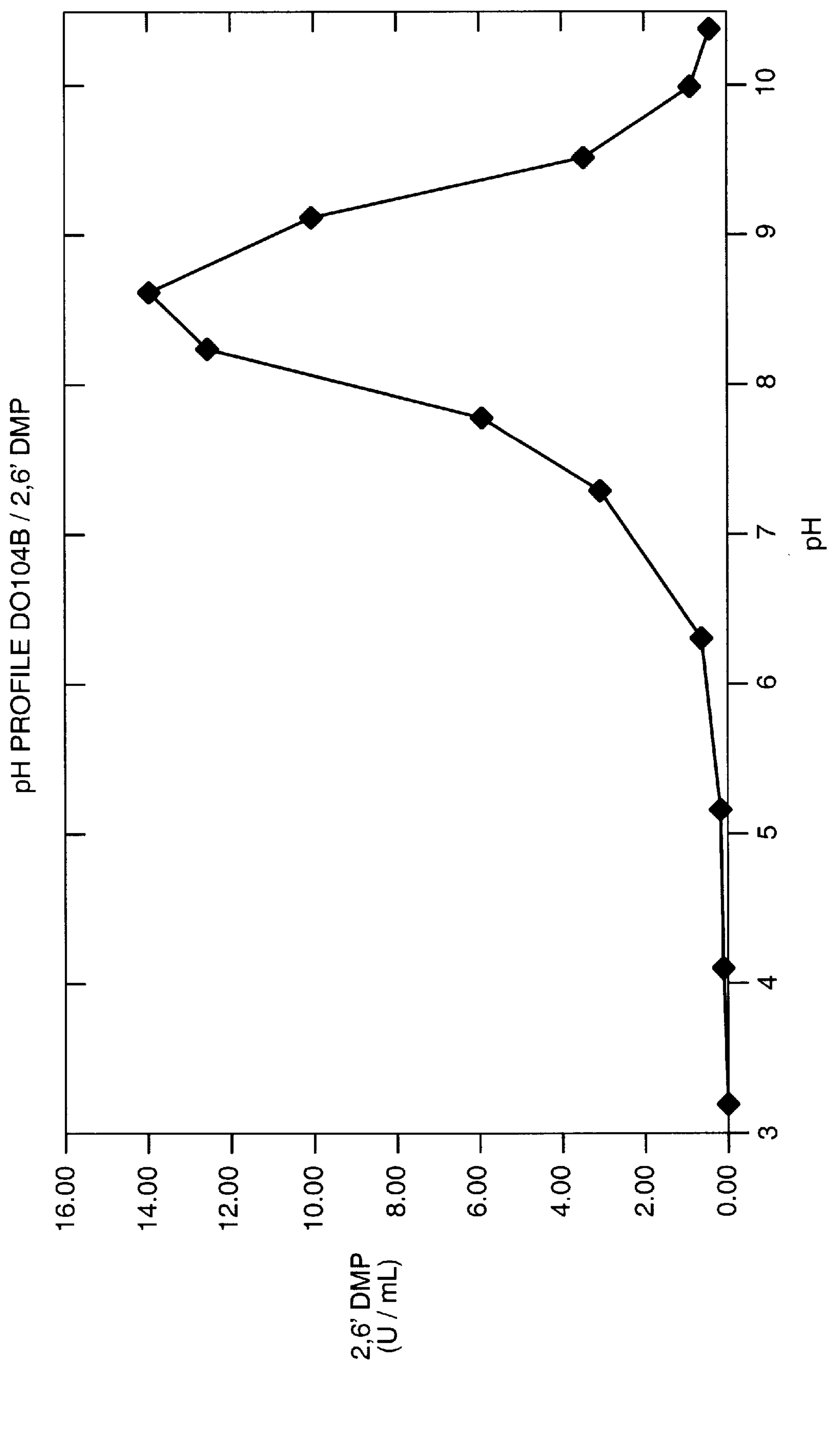
FIG._7

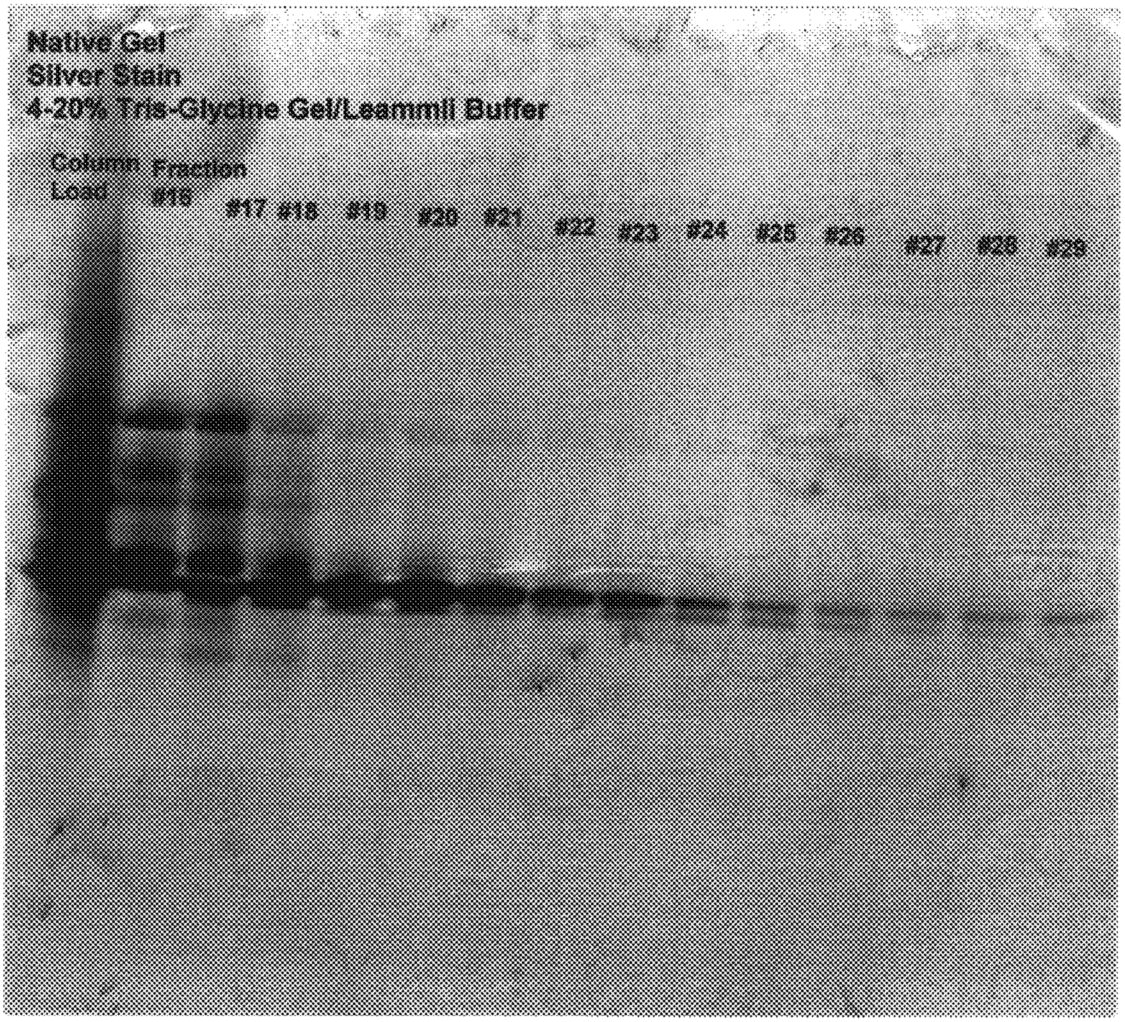
FIG._8

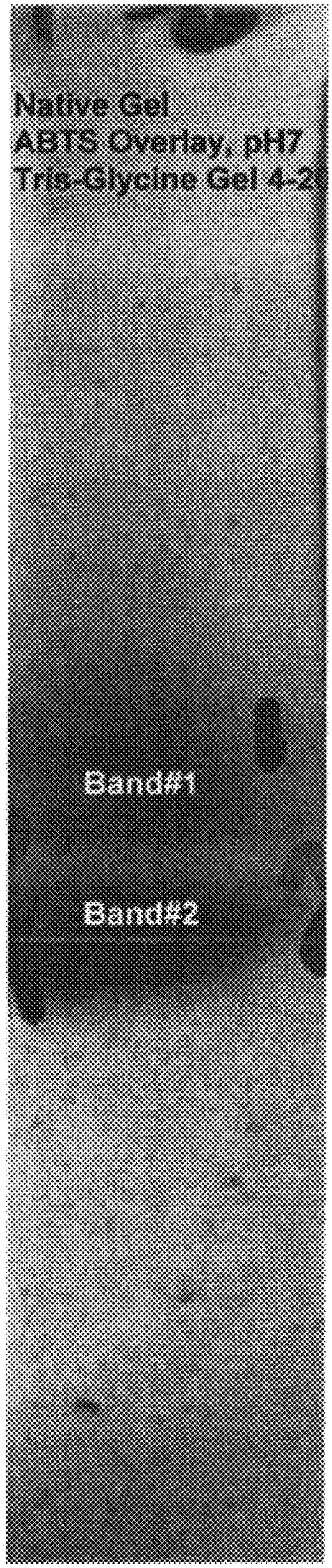
FIG._9

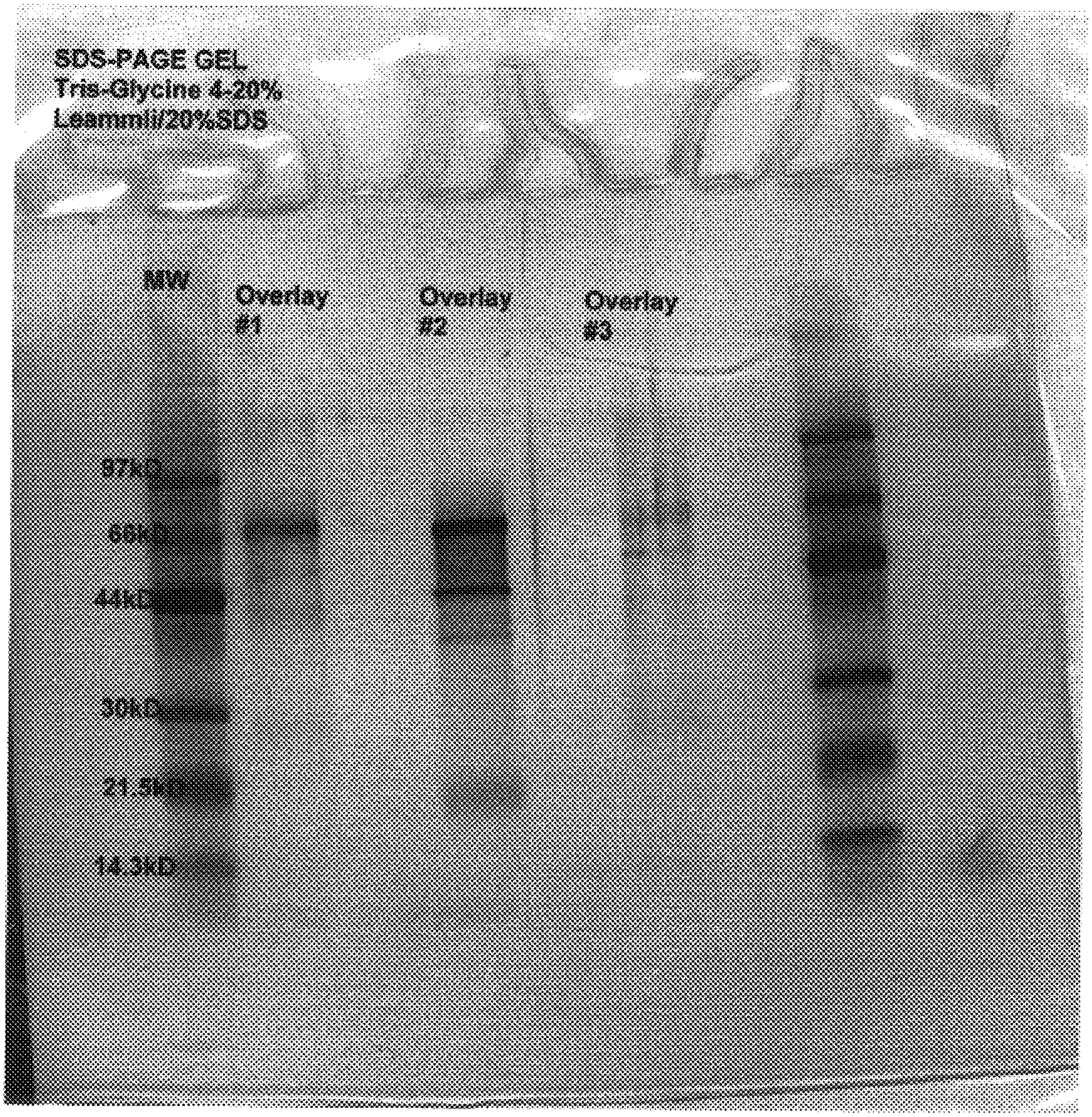
FIG._10

SEQUENCE LISTING

<160> NUMBER OF SEQ ID NOS: 8

<210> SEQ ID NO 1
<211> LENGTH: 1958
<212> TYPE: DNA
<213> ORGANISM: Stachybotrys chararum

<400> SEQUENCE: 1

```
ggatccatca acatgatcag ccaagctatc ggagccgtgg ctctgggcct tgctgtgatc     60
ggcggcagct ctgtcgatgc cagatccgtt gctggtcgat cgacagacat gccttccggt    120
ctcaccaaga ggcagacgca gctgagtcct cccctggcct tgtacgaagt gcctctgccg    180
atccctcctc tgaaggcgcc caagtagtaa gtacattcta taggctagca gagccaacgt    240
tgctaatcat tgcagtaccg tccccaaccc caacactgga gaggacatct tgtactacga    300
gatggagatt aggcccttct cccaccagat ctaccctgat ctggagccgg ccaacatggt    360
tggatacgat ggcatgtccc caggacctac catcatcgtt cctcgtggca ctgagagtgt    420
tgtccgcttc gtgaacagcg gagagaacac ctctcccaac agcgtccact tgcacggctc    480
tttctctcga gctccctttg atggttgggc tgaggacact acccagcctg gcgagtacaa    540
ggattactac taccccaaca ggcaggctgc ccgcatgctt tggtaccatg accatgccat    600
gtccatcacc gccgagaacg cctacatggg tcaggctggt gtctacatga tccaggaccc    660
ggctgaggat gccctgaacc tccccagcgg ctacggcgag tttgatatcc ccttggttct    720
gactgccaag cgatacaacg cagacggcac tctcttctcc accaatggag aggtttccag    780
cttctggggt gacgttattc aagtggtaag ttgagcccat tgagatgctt cagatcctag    840
aagtatcgat gtatgaaatt gtgcatgctc taaccagtgc tatcacagaa cggtcagcct    900
tggcctatgc tcaacgtgca gccgcgcaag taccgcttcc gcttcctcaa cgctgccgtc    960
tcacgctctt tcgctctgta tcttgctacc tctgaggatt cagagaccag acttcccttc   1020
caggtcattg ccgctgacgg tggtctgctt gagggccctg ttgacactga cactctgtac   1080
atctctatgg ccgagcgctg ggaggttgtt atcgacttct ccaccttcgc tggccagtcc   1140
atcgatatcc gcaaccttcc tggtgctgac ggtctcggtg ttgagcctga gtttgataac   1200
actgacaagg tcatgcgatt cgtcgttgat gaagtccttg agtcgcccga cacttctgag   1260
gtgcctgcca acctccgaga tgttcctttc cccgagggcg gcaactggga ccccgcaaac   1320
cccactgatg acgagacttt caccttcggc cgtgctaatg gacagtggac aatcaacgga   1380
gttaccttct cggatgtcga gaaccgtctg ctccgcaatg tgccccgcga cactgttgag   1440
atctggcgac ttgagaacaa ctccaacggt tggactcacc ctgttcacat tcacctcgtt   1500
gacttccgag tcctttctcg ttccactgcc cgtggagtcg agccttatga ggctgctggt   1560
ctcaaggatg ttgtctggct ggctcgtcgt gaggttgtct atgttgaggc ccactacgct   1620
cctttcccgt aagttctcgc cttttaccta actggttttc actcatgcta acatctacaa   1680
gtggtgtcta catgttgcac tgccacaacc tgatccacga ggaccacgac atgatggctg   1740
ctttcaatgt cactgttctc ggtgactatg gctacaacta caccgagttc attgacccca   1800
tggagcctct ctggaggccc cgccccttcc tcctcggaga gttcgagaat ggctcgggtg   1860
acttcagcga gcttgccatc actgaccgca ttcaggagat ggctagcttc aacccctacg   1920
cccaggctga tgatgatgcc gctgaggagt agaccggt                            1958
```

-continued

```
<210> SEQ ID NO 2
<211> LENGTH: 583
<212> TYPE: PRT
<213> ORGANISM: Stachybotrys chartarum

<400> SEQUENCE: 2

Met Ile Ser Gln Ala Ile Gly Ala Val Ala Leu Gly Leu Ala Val Ile
 1               5                  10                  15

Gly Gly Ser Ser Val Asp Ala Arg Ser Val Ala Gly Arg Ser Thr Asp
            20                  25                  30

Met Pro Ser Gly Leu Thr Lys Arg Gln Thr Gln Leu Ser Pro Pro Leu
        35                  40                  45

Ala Leu Tyr Glu Val Pro Leu Pro Ile Pro Pro Leu Lys Ala Pro Asn
    50                  55                  60

Thr Val Pro Asn Pro Asn Thr Gly Glu Asp Ile Leu Tyr Tyr Glu Met
65                  70                  75                  80

Glu Ile Arg Pro Phe Ser His Gln Ile Tyr Pro Asp Leu Glu Pro Ala
                85                  90                  95

Asn Met Val Gly Tyr Asp Gly Met Ser Pro Gly Pro Thr Ile Ile Val
            100                 105                 110

Pro Arg Gly Thr Glu Ser Val Val Arg Phe Val Asn Ser Gly Glu Asn
        115                 120                 125

Thr Ser Pro Asn Ser Val His Leu His Gly Ser Phe Ser Arg Ala Pro
    130                 135                 140

Phe Asp Gly Trp Ala Glu Asp Thr Thr Gln Pro Gly Glu Tyr Lys Asp
145                 150                 155                 160

Tyr Tyr Tyr Pro Asn Arg Gln Ala Ala Arg Met Leu Trp Tyr His Asp
                165                 170                 175

His Ala Met Ser Ile Thr Ala Glu Asn Ala Tyr Met Gly Gln Ala Gly
            180                 185                 190

Val Tyr Met Ile Gln Asp Pro Ala Glu Asp Ala Leu Asn Leu Pro Ser
        195                 200                 205

Gly Tyr Gly Glu Phe Asp Ile Pro Leu Val Leu Thr Ala Lys Arg Tyr
    210                 215                 220

Asn Ala Asp Gly Thr Leu Phe Ser Thr Asn Gly Glu Val Ser Ser Phe
225                 230                 235                 240

Trp Gly Asp Val Ile Gln Val Asn Gly Gln Pro Trp Pro Met Leu Asn
                245                 250                 255

Val Gln Pro Arg Lys Tyr Arg Phe Arg Phe Leu Asn Ala Ala Val Ser
            260                 265                 270

Arg Ser Phe Ala Leu Tyr Leu Ala Thr Ser Glu Asp Ser Glu Thr Arg
        275                 280                 285

Leu Pro Phe Gln Val Ile Ala Ala Asp Gly Gly Leu Leu Glu Gly Pro
    290                 295                 300

Val Asp Thr Asp Thr Leu Tyr Ile Ser Met Ala Glu Arg Trp Glu Val
305                 310                 315                 320

Val Ile Asp Phe Ser Thr Phe Ala Gly Gln Ser Ile Asp Ile Arg Asn
                325                 330                 335

Leu Pro Gly Ala Asp Gly Leu Gly Val Glu Pro Glu Phe Asp Asn Thr
            340                 345                 350

Asp Lys Val Met Arg Phe Val Val Asp Glu Val Leu Glu Ser Pro Asp
        355                 360                 365

Thr Ser Glu Val Pro Ala Asn Leu Arg Asp Val Pro Phe Pro Glu Gly
    370                 375                 380
```

-continued

```
Gly Asn Trp Asp Pro Ala Asn Pro Thr Asp Asp Glu Thr Phe Thr Phe
385                 390                 395                 400

Gly Arg Ala Asn Gly Gln Trp Thr Ile Asn Gly Val Thr Phe Ser Asp
                405                 410                 415

Val Glu Asn Arg Leu Leu Arg Asn Val Pro Arg Asp Thr Val Glu Ile
            420                 425                 430

Trp Arg Leu Glu Asn Asn Ser Asn Gly Trp Thr His Pro Val His Ile
        435                 440                 445

His Leu Val Asp Phe Arg Val Leu Ser Arg Ser Thr Ala Arg Gly Val
    450                 455                 460

Glu Pro Tyr Glu Ala Ala Gly Leu Lys Asp Val Val Trp Leu Ala Arg
465                 470                 475                 480

Arg Glu Val Val Tyr Val Glu Ala His Tyr Ala Pro Phe Pro Gly Val
                485                 490                 495

Tyr Met Leu His Cys His Asn Leu Ile His Glu Asp His Asp Met Met
            500                 505                 510

Ala Ala Phe Asn Val Thr Val Leu Gly Asp Tyr Gly Tyr Asn Tyr Thr
        515                 520                 525

Glu Phe Ile Asp Pro Met Glu Pro Leu Trp Arg Pro Arg Pro Phe Leu
    530                 535                 540

Leu Gly Glu Phe Glu Asn Gly Ser Gly Asp Phe Ser Glu Leu Ala Ile
545                 550                 555                 560

Thr Asp Arg Ile Gln Glu Met Ala Ser Phe Asn Pro Tyr Ala Gln Ala
                565                 570                 575

Asp Asp Asp Ala Ala Glu Glu
            580


<210> SEQ ID NO 3
<211> LENGTH: 2095
<212> TYPE: DNA
<213> ORGANISM: Stachybotrys chararum

<400> SEQUENCE: 3

cagctcggtc tactactctc gcttctcttt gacaaatcaa atctaccaat cgttccttca     60

atttcaaacg atcaacatga tcagccaagc tatcggagcc gtggctctgg gccttgctgt    120

gatcggcggc agctctgtcg atgccagatc cgttgctggt cgatcgacag acatgccttc    180

cggtctcacc aagaggcaga cgcagctgag tcctcccctg gccttgtacg aagtgcctct    240

gccgatccct cctctgaagg cgcccaagta gtaagtacat tctataggct agcagagcca    300

acgttgctaa tcattgcagt accgtcccca accccaacac tggagaggac atcttgtact    360

acgagatgga gattaggccc ttctcccacc agatctaccc tgatctggag ccggccaaca    420

tggttggata cgatggcatg tccccaggac ctaccatcat cgttcctcgt ggcactgaga    480

gtgttgtccg cttcgtgaac agcggagaga acacctctcc caacagcgtc cacttgcacg    540

gctctttctc tcgagctccc tttgatggtt gggctgagga cactacccag cctggcgagt    600

acaaggatta ctactacccc aacaggcagg ctgcccgcat gctttggtac catgaccatg    660

ccatgtccat caccgccgag aacgcctaca tgggtcaggc tggtgtctac atgatccagg    720

acccggctga ggatgccctg aacctcccca gcggctacgg cgagtttgat atccccttgg    780

ttctgactgc caagcgatac aacgcagacg gcactctctt ctccaccaat ggagaggttt    840

ccagcttctg ggtgacgtt attcaagtgg taagttgagc ccattgagat gcttcagatc    900

ctagaagtat cgatgtatga aattgtgcat gctctaacca gtgctatcac agaacggtca    960
```

-continued

```
gccttggcct atgctcaacg tgcagccgcg caagtaccgc ttccgcttcc tcaacgctgc   1020

cgtctcacgc tctttcgctc tgtatcttgc tacctctgag gattcagaga ccagacttcc   1080

cttccaggtc attgccgctg acggtggtct gcttgagggc cctgttgaca ctgacactct   1140

gtacatctct atggccgagc gctgggaggt tgttatcgac ttctccacct tcgctggcca   1200

gtccatcgat atccgcaacc ttcctggtgc tgacggtctc ggtgttgagc ctgagtttga   1260

taacactgac aaggtcatgc gattcgtcgt tgatgaagtc cttgagtcgc ccgacacttc   1320

tgaggtgcct gccaacctcc gagatgttcc tttccccgag ggcggcaact gggaccccgc   1380

aaaccccact gatgacgaga ctttcacctt cggccgtgct aatggacagt ggacaatcaa   1440

cggagttacc ttctcggatg tcgagaaccg tctgctccgc aatgtgcccc gcgacactgt   1500

tgagatctgg cgacttgaga acaactccaa cggttggact caccctgttc acattcacct   1560

cgttgacttc cgagtccttt ctcgttccac tgcccgtgga gtcgagcctt atgaggctgc   1620

tggtctcaag gatgttgtct ggctggctcg tcgtgaggtt gtctatgttg aggcccacta   1680

cgctcctttc ccgtaagttc tcgcctttta cctaactggt tttcactcat gctaacatct   1740

acaagtggtg tctacatgtt gcactgccac aacctgatcc acgaggacca cgacatgatg   1800

gctgctttca atgtcactgt tctcggtgac tatggctaca actacaccga gttcattgac   1860

cccatggagc ctctctggag gccccgcccc ttcctcctcg gagagttcga gaatggctcg   1920

ggtgacttca gcgagcttgc catcactgac cgcattcagg agatggctag cttcaacccc   1980

tacgcccagg ctgatgatga tgccgctgag gagtaaatat gatgatcgtc gaatgattta   2040

tggacagcag tatatagcta ttttaggaaa tacttgaata agttgtggtg cttaa        2095


<210> SEQ ID NO 4
<211> LENGTH: 572
<212> TYPE: PRT
<213> ORGANISM: Stachybotrys charatum

<400> SEQUENCE: 4

Met Phe Lys His Thr Leu Gly Ala Ala Ala Leu Ser Leu Leu Phe Asn
 1               5                  10                  15

Ser Asn Ala Val Gln Ala Ser Pro Val Pro Glu Thr Ser Pro Ala Thr
            20                  25                  30

Gly His Leu Phe Lys Arg Val Ala Gln Ile Ser Pro Gln Tyr Pro Met
        35                  40                  45

Phe Thr Val Pro Leu Pro Ile Pro Pro Val Lys Gln Pro Arg Leu Thr
    50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
    130                 135                 140

Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
                165                 170                 175
```

-continued

```
His Ile Thr Ala Glu Asn Ala Tyr Arg Gly Gln Ala Gly Leu Tyr Met
            180                 185                 190

Leu Thr Asp Pro Ala Glu Asp Ala Leu Asn Leu Pro Ser Gly Tyr Gly
        195                 200                 205

Glu Phe Asp Ile Pro Met Ile Leu Thr Ser Lys Gln Tyr Thr Ala Asn
    210                 215                 220

Gly Asn Leu Val Thr Thr Asn Gly Glu Leu Asn Ser Phe Trp Gly Asp
225                 230                 235                 240

Val Ile His Val Asn Gly Gln Pro Trp Pro Phe Lys Asn Val Glu Pro
                245                 250                 255

Arg Lys Tyr Arg Phe Arg Phe Leu Asp Ala Ala Val Ser Arg Ser Phe
            260                 265                 270

Gly Leu Tyr Phe Ala Asp Thr Asp Ala Ile Asp Thr Arg Leu Pro Phe
        275                 280                 285

Lys Val Ile Ala Ser Asp Ser Gly Leu Leu Glu His Pro Ala Asp Thr
    290                 295                 300

Ser Leu Leu Tyr Ile Ser Met Ala Glu Arg Tyr Glu Val Val Phe Asp
305                 310                 315                 320

Phe Ser Asp Tyr Ala Gly Lys Thr Ile Glu Leu Arg Asn Leu Gly Gly
                325                 330                 335

Ser Ile Gly Gly Ile Gly Thr Asp Thr Asp Tyr Asp Asn Thr Asp Lys
            340                 345                 350

Val Met Arg Phe Val Val Ala Asp Asp Thr Thr Gln Pro Asp Thr Ser
        355                 360                 365

Val Val Pro Ala Asn Leu Arg Asp Val Pro Phe Pro Ser Pro Thr Thr
    370                 375                 380

Asn Thr Pro Arg Gln Phe Arg Phe Gly Arg Thr Gly Pro Thr Trp Thr
385                 390                 395                 400

Ile Asn Gly Val Ala Phe Ala Asp Val Gln Asn Arg Leu Leu Ala Asn
                405                 410                 415

Val Pro Val Gly Thr Val Glu Arg Trp Glu Leu Ile Asn Ala Gly Asn
            420                 425                 430

Gly Trp Thr His Pro Ile His Ile His Leu Val Asp Phe Lys Val Ile
        435                 440                 445

Ser Arg Thr Ser Gly Asn Asn Ala Arg Thr Val Met Pro Tyr Glu Ser
    450                 455                 460

Gly Leu Lys Asp Val Val Trp Leu Gly Arg Arg Glu Thr Val Val Val
465                 470                 475                 480

Glu Ala His Tyr Ala Pro Phe Pro Gly Val Tyr Met Phe His Cys His
                485                 490                 495

Asn Leu Ile His Glu Asp His Asp Met Met Ala Ala Phe Asn Ala Thr
            500                 505                 510

Val Leu Pro Asp Tyr Gly Tyr Asn Ala Thr Val Phe Val Asp Pro Met
        515                 520                 525

Glu Glu Leu Trp Gln Ala Arg Pro Tyr Glu Leu Gly Glu Phe Gln Ala
    530                 535                 540

Gln Ser Gly Gln Phe Ser Val Gln Ala Val Thr Glu Arg Ile Gln Thr
545                 550                 555                 560

Met Ala Glu Tyr Arg Pro Tyr Ala Ala Ala Asp Glu
                565                 570
```

<210> SEQ ID NO 5
<211> LENGTH: 21
<212> TYPE: PRT

-continued

```
<213> ORGANISM: Artificial Sequence
<220> FEATURE:
<223> OTHER INFORMATION: Primer

<400> SEQUENCE: 5

Phe Val Asn Ser Gly Glu Asn Thr Ser Pro Asn Ser Val His Leu His
 1              5                   10                  15

Gly Ser Phe Ser Arg
            20


<210> SEQ ID NO 6
<211> LENGTH: 18
<212> TYPE: PRT
<213> ORGANISM: Artificial Sequence
<220> FEATURE:
<223> OTHER INFORMATION: Primer

<400> SEQUENCE: 6

Gly Val Glu Pro Tyr Glu Ala Ala Gly Leu Lys Asp Val Val Trp Leu
 1              5                   10                  15

Ala Arg


<210> SEQ ID NO 7
<211> LENGTH: 20
<212> TYPE: DNA
<213> ORGANISM: Stachybotrys chartarum

<400> SEQUENCE: 7

gtcaacagtg gngaraayac                                              20


<210> SEQ ID NO 8
<211> LENGTH: 20
<212> TYPE: DNA
<213> ORGANISM: Stachybotrys chartarum

<400> SEQUENCE: 8

gcggcctcat anggctcnac                                              20
```

PHENOL OXIDIZING ENZYMES

FIELD OF THE INVENTION

The present invention relates to novel phenol oxidizing enzymes, in particular, novel phenol oxidizing enzymes derived from strains of *Stachybotrys* and novel strains of the genus Stachybotrys producing these enzymes. The present invention provides methods and host cells for expressing *Stachybotrys* phenol oxidizing enzymes as well as methods for producing expression systems.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to $H_2O$. While being capable of using a wide variety of different phenolic compounds as electron donors, phenol oxidizing enzymes are very specific for molecular oxygen as the electron acceptor.

Phenol oxidizing enzymes can be utilized for a wide variety of applications, including the detergent industry, the paper and pulp industry, the textile industry and the food industry. In the detergent industry, phenol oxidizing enzymes have been used for preventing the transfer of dyes in solution from one textile to another during detergent washing, an application commonly referred to as dye transfer inhibition.

Most phenol oxidizing enzymes exhibit pH optima in the acidic pH range while being inactive in neutral or alkaline pHs.

Phenol oxidizing enzymes are known to be produced by a wide variety of fungi, including species of the genii Aspergillus, Neurospora, Podospora, Botytis, Pleurotus, Fomes, Phlebia, Trametes, Polyporus, Rhizoctonia and Lentinus. However, there remains a need to identify and isolate phenol oxidizing enzymes, and organisms capable of naturally-producing phenol oxidizing enzymes, which present pH optima in the alkaline range for use in detergent washing methods and compositions.

SUMMARY OF THE INVENTION

The present invention relates to novel phenol oxidizing enzymes. In a preferred embodiment, the present invention relates to phenol oxidizing enzymes obtainable from *Stachybotrys*. In particular, the enzymes of the present invention are capable of modifying the color associated with dyes and colored compounds having different chemical structures, especially at neutral or alkaline pH. Based on their color modifying ability, phenol oxidizing enzymes of the present invention can be used, for example, for pulp and paper bleaching, for bleaching the color of stains on fabric and in detergent and textile applications. In one aspect of the present invention, the phenol oxidizing enzyme is able to modify the color of a dye or colored compound in the absence of an enhancer. In another aspect of the present invention, the phenol oxidizing enzyme is able to modify the color in the presence of an enhancer.

The present invention is based upon the identification and characterization of a genomic sequence (SEQ ID NO:3) encoding a phenol oxidizing enzyme obtainable from *Stachybotrys* and having the deduced amino acid sequence as shown in SEQ ID NO:2.

Accordingly, the present invention provides phenol oxidizing enzymes comprising between at least 68% and 100% identity, that is, at least 68% identity, at least 70%, at least 75% identity, at least 80% identity, at least 85% identity, at least 90% identity and at least 95% identity to the phenol oxidizing enzyme having the amino acid sequence disclosed in SEQ ID NO:2, as long as the enzyme is capable of modifying the color associated with dyes or colored compounds. In one embodiment, the phenol oxidizing enzyme has the amino acid sequence as shown in SEQ ID NO:2 or as contained in *Stachybotrys chartarum* having MUCL accession number 38898.

In one embodiment, the phenol oxidizing enzyme is obtainable from a *Stachybotrys* species including *Stachybotrys parvispora, Stachybotrys chartarum; S. kampalensis; S. theobromae; S. bisbyi, S. cylindrospora, S. dichroa, S. oenanthes* and *S. nilagerica*. In another embodiment, the *Stachybotrys* includes *Stachybotrys chartarum* MUCL 38898 and *S. chartarum* MUCL 30782.

In yet another embodiment, the present invention provides an isolated polynucleotide encoding a phenol oxidizing enzyme wherein said polynucleotide comprises a nucleic acid sequence having between at least 65% and 100% identity, that is, at least 65% identity, at least 70%, at least 75% identity, at least 80%, at least 85%, at least 90% and at least 95% identity to SEQ ID NO:1, as long as the polynucleotide encodes a phenol oxidizing enzyme capable of modifying the color associated with dyes or colored compounds. The present invention encompasses polynucleotide sequences that hybridize under conditions of high stringency to the polynucleotide shown in SEQ ID NO:1 or SEQ ID NO:3 as long as the sequence is capable of modifying the color associated with dyes or colored compounds. The present invention also encompasses polynucleotides that encode the amino acid sequence as shown in SEQ ID NO:2. In one embodiment, the polynucleotide has the nucleic acid sequence as shown in SEQ ID NO: 1 or SEQ ID NO:3 or as contained in *Stachybotrys chartarum* having MUCL accession number 38898. The present invention also provides expression vectors and host cells comprising polynucleotides of the present invention.

The present invention additionally relates to methods for producing a phenol oxidizing enzyme of the present invention. Accordingly, the present invention provides a method for producing a phenol oxidizing enzyme comprising the step of culturing a host cell comprising an isolated polynucleotide encoding a phenol oxidizing enzyme having a sequence comprising between at least 68% and 100% identity, that is, at least 68% identity, at least 70%, at least 75% identity, at least 80% identity, at least 85% identity, at least 90% identity and at least 95% identity to the phenol oxidizing enzyme having the amino acid sequence disclosed in SEQ ID NO:2 under conditions suitable for the production of said phenol oxidizing enzyme; and optionally recovering said phenol oxidizing enzyme produced. In one embodiment, the polynucleotide comprises the sequence as shown in SEQ ID NO:1. In another embodiment, the polynucleotide comprises the sequence as shown in SEQ ID NO: 3. In an additional embodiment, the polynucleotide hybridizes under conditions of high stringency with the polynucleotide having the sequence as shown in SEQ ID NO:1 or SEQ ID NO:3 or as contained in *Stachybotrys chartarum* having MUCL accession number 38898. In a further embodiment, the polynucleotide has between 65% and 100%, that is, at least 65% identity, at least 70%, at least 75% identity, at least 80% identity, at least 85% identity, at least 90% identity and at least 95% identity to SEQ ID NO: 1 or SEQ ID NO:3.

The present invention also provides a method for producing a recombinant host cell comprising a polynucleotide encoding a phenol oxidizing enzyme, comprising the steps of obtaining an isolated polynucleotide encoding said phenol oxidizing enzyme said polynucleotide having between at least 65% and 100% identity, that is, at least 65% identity, at least 70%, at least 75% identity, at least 80%, at least 85%, at least 90% and at least 95% identity to SEQ ID NO:3; introducing said polynucleotide into said host cell; and growing said host cell under conditions suitable for the production of said phenol oxidizing enzyme. In one embodiment, the polynucleotide is integrated into the host genome and in another embodiment, the polynucleotide is present on a replicating plasmid. The present invention also encompasses polynucleotide sequences that hybridize under conditions of high stringency to the polynucleotide shown in SEQ ID NO:1 or SEQ ID NO:3. The present invention also provides polynucleotides that encode the amino acid sequence as shown in SEQ ID NO:2. In one embodiment, the polynucleotide has the nucleic acid sequence as shown in SEQ ID NO:1 or SEQ ID NO:3 or as contained in *Stachybotrys chartarum* having MUCL accession number 38898.

In one embodiment of the present invention, the host cell comprising a polynucleotide encoding a phenol oxidizing enzyme includes filamentous fungus, yeast and bacteria. In another embodiment, the host cell is a filamentous fungus including *Aspergillus* species , *Trichoderma* species and *Mucor* species. In an additional embodiment, the filamentous fungus host cell includes *Aspergillus niger* var. *awamori* and *Trichoderma reseei.*

In another embodiment of the present invention, the host cell is a yeast which includes *Saccharomyces, Pichia, Hansenula, Schizosaccharomyces, Kluyveromyces* and *Yarrowia* species. In yet another embodiment, the *Saccharomyces* species is *Saccharomyces cerevisiae*. In an additional embodiment, the host cell is a bacteria including gram positive bacteria, such as a *Bacillus* species, and gram negative bacteria, such as an *Escherichia* species.

Also provided herein are enzymatic compositions comprising the amino acid having between at least 68% and 100% identity, that is, at least 68% identity, at least 70%, at least 75% identity, at least 80% identity, at least 85% identity, at least 90% identity and at least 95% identity to the phenol oxidizing enzyme having the amino acid sequence disclosed in SEQ ID NO:2. In one embodiment, the amino acid has the sequence as shown in SEQ ID NO: 2. Such enzymatic compositions can be used, for example, for producing detergents and other cleaning compositions; compositions for use in pulp and paper applications; and textile applications.

The present invention also encompasses methods for modifying the color associated with dyes or colored compounds which occur in stains on samples, comprising the steps of contacting the sample with a composition comprising an amino acid having a sequence between at least 68% and 100% identity, that is, at least 68% identity, at least 70%, at least 75% identity, at least 80% identity, at least 85% identity, at least 90% identity and at least 95% identity to the phenol oxidizing enzyme having the amino acid sequence disclosed in SEQ ID NO:2, as long as the enzyme is capable of modifying the color associated with dyes or colored compounds. In a preferred embodiment of the method, the amino acid is that shown in SEQ ID NO:2.

In one aspect of the method, the pH optimum is between 5.0 and 11.0, in another aspect, the pH optimum is between 7 and 10.5 and in yet another aspect the pH optimum is between 8.0 and 10. In a further aspect of the method, the optimum temperature is between 20 and 60 degrees C. and in another aspect between 20 and 40 degrees C.

BRIEF DESCRIPTION OF THE DRAWINGS

FIG. 1 provides the nucleic acid sequence (SEQ ID NO:1) for a phenol oxidizing enzyme obtainable from *Stachybotrys chartarum* by PCR as described in Example 5.

FIG. 2 provides the amino acid sequence (SEQ ID NO:2) for the amino acid designated herein as the *Stachybotrys* oxidase B gene.

FIG. 3 illustrates the genomic sequence (SEQ ID NO:3) for a phenol oxidizing enzyme obtainable from *Stachybotrys chartarum*. This nucleic acid sequence is referred to herein as *Stachybotrys* oxidase B gene.

FIG. 4 is an amino acid alignment of *Stachybotrys* phenol oxidase B enzyme SEQ ID NO:2 (bottom line) and *Bilirubin* oxidase (SEQ ID NO:4).

FIG. 5 provides an illustration of the vector pGAPT2-spoB which was used for the expression of *Stachybotrys* phenol oxidizing enzyme in *Aspergillus*. Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. The rest of the plasmid contains pBR322 sequences for propagation in *E. coli*. Nucleic acid encoding the *Stachybotrys* phenol oxidizing enzyme of SEQ ID NO:1 was cloned into the Bgl II and Age I restriction sites.

FIG. 6 is an illustration of expression of the *Stachybotrys* oxidase B protein in a replicating plasmid. The *Stachybotrys* oxidase expression is under the *Aspergillus glucoamylase* promoter and terminator control. The transformation marker pyrG gene and the AMA 1 sequence are from *Aspergillus nidulans.*

FIG. 7 shows the pH profile for *Stachybotrys* oxidase B against the substrate 2,6 DMP.

FIG. 8 shows a non-denatured (native) gel electrophoresis of *Stachybotrys chartarum* fractions from an ion exchange column (silver stained) as described in Example 1.

FIG. 9 shows a non-denatured gel electrophoresis of fractions with ABTS overlay as described in Example 1.

FIG. 10 shows an SDS-PAGE gel of bands identified and isolated from an ABTS overlay of the gel shown in FIG. 9. *Stachybotrys chartarum* oxidase B is shown in the lane labeled Overlay 2. Lane Overlay 2 shows the observed banding pattern for *Stachybotrys chartarum* oxidase B under the conditions described.

DETAILED DESCRIPTION

Definitions

As used herein, the term phenol oxidizing enzyme refers to those enzymes which are capable of catalyzing redox reactions wherein the electron donor is a phenolic compound and which are specific for molecular oxygen or hydrogen peroxide as the electron acceptor. One illustrative phenol oxidizing enzyme of the present invention obtainable from *Stachybotrys chartarum* is shown in SEQ ID NO:2. The present invention encompasses phenol oxidizing enzymes that have between at least 68% and 100% identity, that is, at least 68% identity, at least 70%, at least 75% identity, at least 80% identity, at least 85% identity, at least 90% identity and at least 95% identity to the phenol oxidizing enzyme having the amino acid sequence disclosed in SEQ ID NO:2. As used herein, identity is measured by the GAP program of GCG software (University Research Park, Madison Wis.) with the following parameters: Gap Weight=12; Length Weight=4; Gap Creation Penalty=8; and Gap Extension Penalty=2.

As used herein, *Stachybotrys* refers to any *Stachybotrys* species which produces a phenol oxidizing enzyme capable of modifying the color associated with dyes or colored compounds. The present invention encompasses derivatives of natural isolates of *Stachybotrys*, including progeny and mutants, as long as the derivative is able to produce a phenol oxidizing enzyme capable of modifying the color associated with dye or color compounds.

As used herein in referring to phenol oxidizing enzymes, the term "obtainable from" means phenol oxidizing enzymes that originate from or are naturally-produced by the particular microbial strain mentioned. To exemplify, phenol oxidizing enzymes obtainable from *Stachybotrys* refer to those phenol oxidizing enzymes which are naturally-produced by *Stachybotrys*. The present invention encompasses phenol oxidizing enzymes identical to those produced by *Stachybotrys* species but which are produced through the use of genetic engineering techniques by organisms, such as bacteria, fungus or yeast, transformed with a gene encoding said phenol oxidizing enzyme or produced by organisms which are identical to those from *Stachybotrys*, or equivalent to those from *Stachybotrys*, such as progeny or mutants.

The present invention encompasses phenol oxidizing enzymes encoded by a polynucleotide capable of hybridizing to the polynucleotide having the sequence as shown in SEQ ID NO:1 or SEQ ID NO:3 under conditions of high stringency. The present invention encompasses polynucleotides encoding phenol oxidizing enzymes which comprises at least 65% identity, at least 70%, at least 75% identity, at least 80% identity, at least 85% identity, at least 90% identity or at least 95% identity to the polynucleotide having the sequence as disclosed in SEQ ID NO:1. Identity at the nucleic acid level is measured by the GAP program of the GCG Software (University Research Park, Madison, Wis.) with the following parameters: Gap Weight=50; Length Weight=4; Gap Creation Penalty=50; and Gap Extension Penalty=3. The present invention also encompasses mutants, variants and derivatives, including portions, of the phenol oxidizing enzymes of the present invention as long as the mutant, variant or derivative phenol oxidizing enzyme is able to retain at least one characteristic activity of the naturally occurring phenol oxidizing enzyme.

As used herein, the term 'colored compound' refers to a substance that adds color to textiles or to substances which result in the visual appearance of stains. As defined in Dictionary of Fiber and Textile Technology (Hoechst Celanese Corporation (1990) PO Box 32414, Charlotte N.C. 28232), a dye is a colored compound that is incorporated into the fiber by chemical reaction, absorption, or dispersion. Examples of dyes include direct Blue dyes, acid Blue dyes, direct red dyes, reactive Blue and reactive Black dyes. A catalogue of commonly used textile dyes is found in Colour Index, 3$^{rd}$ ed. Vol. 1–8. Examples of substances which result in the visual appearance of stains are polyphenols, carotenoids, anthocyanins, tannins, Maillard reaction products, etc.

As used herein the phrase "modify the color associated with a dye or colored compound" or "modification of the colored compound" means that the dye or compound is changed through oxidation, either directly or indirectly, such that either the color appears modified, i.e., the color visually appears to be decreased, lessened, decolored, bleached or removed, or the color is not affected but the compound is modified such that dye redeposition is inhibited. The present invention encompasses the modification of the color by any means including, for example, the complete removal of the colored compound from stain on a fabric by any means as well as a reduction of the color intensity or a change in the color of the compound.

As used herein, the term "mutants and variants", when referring to phenol oxidizing enzymes, refers to phenol oxidizing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phenol oxidizing enzyme. The term phenol oxidizing enzyme "derivative" as used herein refers to a portion or fragment of the full-length naturally occurring or variant phenol oxidizing enzyme amino acid sequence that retains at least one activity of the naturally occurring phenol oxidizing enzyme. As used herein, the term "mutants and variants", when referring to microbial strains, refers to cells that are changed from a natural isolate in some form, for example, having altered DNA nucleotide sequence of, for example, the structural gene coding for the phenol oxidizing enzyme; alterations to a natural isolate in order to enhance phenol oxidizing enzyme production; or other changes that effect phenol oxidizing enzyme expression.

The term "enhancer" or "mediator" refers to any compound that is able to modify the color associated with a dye or colored compound in association with a phenol oxidizing enzyme or a compound which increases the oxidative activity of the phenol oxidizing enzyme. The enhancing agent is typically an organic compound.

Phenol Oxidizing Enzymes

The phenol oxidizing enzymes of the present invention function by catalyzing redox reactions, i.e., the transfer of electrons from an electron donor (usually a phenolic compound) to molecular oxygen or hydrogen peroxide (which acts as an electron acceptor) which is reduced to water. Examples of such enzymes are laccases (EC 1.10.3.2), bilirubin oxidases (EC 1.3.3.5), phenol oxidases (EC 1.14.18.1), catechol oxidases (EC 1.10.3.1).

Nucleic Acid Encoding Phenol Oxidizing Enzymes

The present invention encompasses polynucleotides which encode phenol oxidizing enzymes obtainable from *Stachybotrys* species which polynucleotides comprise between at least 65% and 100% identity, that is at least 65% identity, at least 70% identity, at least 75% identity, at least 80% identity, at least 85% identity, at least 90% identity and at least 95% identity to the polynucleotide sequence disclosed in SEQ ID NO:3 as long as the enzyme encoded by the polynucleotide is capable of modifying the color associated with dyes or colored compounds. In one embodiment, the phenol oxidizing enzyme has the polynucleotide sequence as shown in SEQ ID NO:3 or SEQ ID NO:1 or has the polynucleotide sequence as contained in *Stachybotrys chartarum* having MUCL accession number 38898. As will be understood by the skilled artisan, due to the degeneracy of the genetic code, a variety of polynucleotides can encode the phenol oxidizing enzyme disclosed in SEQ ID NO: 2. The present invention encompasses all such polynucleotides.

The nucleic acid encoding a phenol oxidizing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a *Stachybotrys* species (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II) Nucleic acid sequences derived from genomic DNA may contain regulatory regions in addition to coding regions. Whatever the source, the isolated nucleic acid encoding a phenol oxidizing enzyme of the present invention should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, and column chromatography.

Once nucleic acid fragments are generated, identification of the specific DNA fragment encoding a phenol oxidizing enzyme may be accomplished in a number of ways. For example, a phenol oxidizing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under high stringency conditions.

The present invention encompasses phenol oxidizing enzymes obtainable from *Stachybotrys* species which are identified through nucleic acid hybridization techniques using SEQ ID NO:1 or SEQ ID NO:3 as a probe or primer and screening nucleic acid of either genomic or cDNA origin. Nucleic acid encoding phenol oxidizing enzymes obtainable from *Stachybotrys* species and having at least 65% identity to SEQ ID NO:1 or SEQ ID NO:3 can be detected by DNA—DNA or DNA-RNA hybridization or amplification using probes, portions or fragments of SEQ ID NO:1 or SEQ ID NO:3. Accordingly, the present invention provides a method for the detection of nucleic acid encoding a phenol oxidizing enzyme encompassed by the present invention which comprises hybridizing part or all of a nucleic acid sequence of SEQ ID NO:1 or SEQ ID NO:3 with *Stachybotrys* nucleic acid of either genomic or cDNA origin.

Accordingly, included within the scope of the present invention are polynucleotide sequences that are capable of hybridizing to the nucleotide sequence disclosed in SEQ ID NO:3 under conditions of high stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined "stringency" as explained below.

"Maximum stringency" typically occurs at about Tm−5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. For example in the present invention the following are the conditions for high stringency: hybridization was done at 37° C. in buffer containing 50% formamide, 5×SSPE, 0.5% SDS and 50 ug/ml of sheared Herring DNA. The washing was performed at 65° C. for 30 minutes in the presence of 1×SSC and 0.1% SDS once, at 65° C. for 30 minutes in presence of 0.5× SSC and 0.1% SDS once and at 65° C. for 30 minutes in presence of 0.1×SSC and 0.1% SDS once; the following are the conditions for intermediate stringency: hybridization was done at 37° C. in buffer containing 25% formamide, 5× SSPE, 0.5% SDS and 50 ug/ml of sheared Herring DNA. The washing was performed at 50° C. for 30 minutes in presence of 1× SSC and 0.1% SDS once, at 50° C. for 30 minutes in presence of 0.5× SSC and 0.1% SDS once; the following are the conditions for low stringency: hybridization was done at 37° C. in buffer containing 25% formamide, 5× SSPE, 0.5% SDS and 50 ug/ml of sheared Herring DNA. The washing was performed at 37° C. for 30 minutes in presence of 1× SSC and 0.1% SDS once, at 37° C. for 30 minutes in presence of 0.5× SSC and 0.1% SDS once. A nucleic acid capable of hybridizing to a nucleic acid probe under conditions of high stringency will have about 80% to 100% identity to the probe; a nucleic acid capable of hybridizing to a nucleic acid probe under conditions of intermediate stringency will have about 50% to about 80% identity to the probe.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from SEQ ID NO:3 preferably about 12 to 30 nucleotides, and more preferably about 25 nucleotides can be used as a PCR primer.

A preferred method of isolating a nucleic acid construct of the invention from a cDNA or genomic library is by use of polymerase chain reaction (PCR) using degenerate oligonucleotide probes prepared on the basis of the amino acid sequence of the protein having the amino acid sequence as shown in SEQ ID NO:2. For instance, the PCR may be carried out using the techniques described in U.S. Pat. No. 4,683,202.

Expression Systems

The present invention provides host cells, expression methods and systems for the production of phenol oxidizing enzymes in host microorganisms, such as fungus, yeast and bacteria. Once nucleic acid encoding a phenol oxidizing enzyme of the present invention is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding phenol oxidizing enzymes having between at least 65% and 100%, at least 65%, at least 70%, at least 75%, at least 80%, at least 85%, at least 90% and at least 95% identity to the nucleic acid of SEQ ID NO:1 or SEQ ID NO:3 as measured by the GAP program of the GCG Software (University Research Park, Madison, Wis.) with the following parameters: Gap Weight=50; Length Weight=4; Gap Creation Penalty=50; and Gap Extension Penalty=3 is obtained and transformed into a host cell using appropriate vectors. A variety of vectors and transformation and expression cassettes suitable for the cloning, transformation and expression in fungus, yeast and bacteria are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phenol oxidizing enzymes in a host cell are known to those skilled in the art. Virtually any promoter capable of driving these phenol oxidizing enzyme is suitable for the present invention. Nucleic acid encoding the phenol oxidizing enzyme is linked operably through initiation codons to selected expression control regions for effective expression of the oxidative or reducing enzymes. Once suitable cassettes are constructed they are used to transform the host cell.

General transformation procedures are taught in Current Protocols In Molecular Biology (vol.1, edited by Ausubel et al., John Wiley & Sons, Inc. 1987, Chapter 9) and include calcium phosphate methods, transformation using PEG and electroporation. For *Aspergillus* and *Trichoderma*, PEG and Calcium mediated protoplast transformation can be used (Finkelstein, D B 1992 Transformation. In Biotechnology of Filamentous Fungi. Technology and Products (eds by Finkelstein & Bill) 113–156. Electroporation of protoplast is disclosed in Finkelestein, DB 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia. FEMS Microbiology Letters 125 293–298. Agrobacterium mediated transformation is disclosed in Groot et al. (1998) *Agrobacterium tumefaciens*-mediated transformation of filamentous fungi. Nature Biotechnology 16 839–842. For transformation of *Saccharomyces*, lithium acetate mediated transformation and PEG and calcium mediated protoplast transformation as well as electroporation techniques are known by those of skill in the art.

Host cells which contain the coding sequence for a phenol oxidizing enzyme of the present invention and express the protein may be identified by a variety of procedures known to those of skill in the art. These procedures include, but are not limited to, DNA—DNA or DNA-RNA hybridization and protein bioassay or immunoassay techniques which include membrane-based, solution-based, or chip-based technologies for the detection and/or quantification of the nucleic acid or protein.

As described herein, the genomic sequence (SEQ ID NO:3) encoding phenol oxidizing enzyme obtainable from *Stachybotrys chartarum* (MUCL 38898) was isolated and expressed in *Aspergillus niger* var. *awamori* and *Trichoderma reesei.*

Phenol Oxidizing Enzyme Activities

The phenol oxidizing enzymes of the present invention are capable of using a wide variety of different phenolic compounds as electron donors, while being very specific for molecular oxygen or hydrogen peroxide as the electron acceptor.

Depending upon the specific substrate and reaction conditions, e.g., temperature, presence or absence of enhancers, etc., each phenol oxidizing enzyme oxidation reaction will have an optimum pH.

Applications Of Polyphenol Oxidizing Enzymes

As described infra, the *Stachybotrys* phenol oxidizing enzymes of the present invention are capable of oxidizing a wide variety of dyes or colored compounds having different chemical structures, using oxygen or hydrogen peroxide as the electron acceptor. Accordingly phenol oxidizing enzymes of the present invention are used in applications where it is desirable to modify the color associated with dyes or colored compounds, such as in cleaning, for removing the food stains on fabric; and for textiles; and paper and pulp applications. A mediator or enhancer may be needed to obtain desirable effects.

Colored Compounds

In the present invention, a variety of colored compounds could be targets for oxidation by phenol oxidizing enzymes of the present invention. For example, in detergent applications, colored substances which may occur as stains on fabrics can be a target. Several types or classes of colored substances may appear as stains, such as porphyrin derived structures, such as heme in blood stain or chlorophyll in plants; tannins and polyphenols (see P. Ribéreau-Gayon, Plant Phenolics, Ed. Oliver & Boyd, Edinburgh, 1972, pp.169–198) which occur in tea stains, wine stains, banana stains, peach stains; carotenoids, the coloured substances which occur in tomato (lycopene, red), mango (carotene, orange-yellow) (G. E. Bartley et al., The Plant Cell (1995), Vol 7, 1027–1038); anthocyanins, the highly colored molecules which occur in many fruits and flowers (P. Ribéreau-Gayon, Plant Phenolics, Ed. Oliver & Boyd, Edinburgh, 1972, 135–169); and Maillard reaction products, the yellow/brown colored substances which appear upon heating of mixtures of carbohydrate molecules in the presence of protein/peptide structures, such as found in cooking oil.

Enhancers

A phenol oxidizing enzyme of the present invention can act to modify the color associated with dyes or colored compounds in the presence or absence of enhancers depending upon the characteristics of the compound. If a compound is able to act as a direct substrate for the phenol oxidizing enzyme, the phenol oxidizing enzyme will modify the color associated with a dye or colored compound in the absence of an enhancer, although an enhancer may still be preferred for optimum phenol oxidizing enzyme activity. For other colored compounds unable to act as a direct substrate for the phenol oxidizing enzyme or not directly accessible to the phenol oxidizing enzyme, an enhancer is required for optimum phenol oxidizing enzyme activity and modification of the color.

Enhancers are described in for example WO 95/01426 published Jan. 12, 1995; WO 96/06930, published Mar. 7, 1996; and WO 97/11217 published Mar. 27, 1997. Enhancers include but are not limited to phenothiazine-10-propionic acid (PTP), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis (3-ethylbenzothiazoline-6-sulfonate (ABTS).

Cultures

The present invention encompasses *Stachybottys* strains and natural isolates, and derivatives of such strains and isolates, such as strains of the species *Stachybotrys parvispora*, including, in particular, *Stachybotrys parvispora* var. hughes MUCL 38996; strains of the species *Stachybotrys chartarum* including, in particular, *Stachybotrys chartarum* MUCL 38898; *S. parvispora* MUCL 9485; *S. chartarum* MUCL 30782; *S. kampalensis* MUCL 39090; *S. theobromae* MUCL 39293; and strains of the species *S.*

*bisbyi, S. cylindrospora, S. dichroa, S. oenanthes* and *S. nilagerica* which produce phenol oxidizing enzymes of the present invention.

The present invention provides substantially biologically-pure cultures of novel strains of the genus Stachybotrys, and, in particular substantially biologically-pure cultures of the strains *Stachybotrys parvispora* MUCL 38996 and *Stachybotrys chartarum* MUCL 38898 from which phenol oxidizing enzymes can be purified.

Purification

The phenol oxidizing enzymes of the present invention may be produced by cultivation of phenol oxidizing enzyme-producing *Stachybotrys* strains (such as *S. parvispora* MUCL 38996, *S. chartarum* MUCL 38898) under aerobic conditions in nutrient medium containing assimiable carbon and nitrogen together with other essential nutrient(s). The medium can be composed in accordance with principles well-known in the art.

During cultivation, the phenol oxidizing enzyme-producing strains secrete phenol oxidizing enzyme extracellularly. This permits the isolation and purification (recovery) of the phenol oxidizing enzyme to be achieved by, for example, separation of cell mass from a culture broth (e.g. by filtration or centrifugation). The resulting cell-free culture broth can be used as such or, if desired, may first be concentrated (e.g. by evaporation or ultrafiltration). If desired, the phenol oxidizing enzyme can then be separated from the cell-free broth and purified to the desired degree by conventional methods, e.g. by column chromatography.

The phenol oxidizing enzymes of the present invention may be isolated and purified from the culture broth into which they are extracellularly secreted by concentration of the supernatant of the host culture, followed by ammonium sulfate fractionation and gel permeation chromatography.

The phenol oxidizing enzymes of the present invention may be formulated and utilized according to their intended application. In this respect, if being used in a detergent composition, the phenol oxidizing enzyme may be formulated, directly from the fermentation broth, as a coated solid using the procedure described in U.S. Pat. No. 4,689,297. Furthermore, if desired, the phenol oxidizing enzyme may be formulated in a liquid form with a suitable carrier. The phenol oxidizing enzyme may also be immobilized, if desired.

The present invention also encompasses expression vectors and recombinant host cells comprising a *Stachybotrys* phenol oxidizing enzyme of the present invention and the subsequent purification of the phenol oxidizing enzyme from the recombinant host cell.

Enzyme Compositions

A phenol oxidizing enzyme of the present invention may be used to produce, for example, enzymatic compositions for use in detergent or cleaning compositions; in textiles, that is in the treatment, processing, finishing, polishing, or production of fibers; in the production of paper and pulp; and in starch processing applications. Enzymatic compositions may also comprise additional components, such as for example, for formulation or as performance enhancers For example, detergent composition may comprise, in addition to the phenol oxidizing enzyme, conventional detergent ingredients such as surfactants, builders and further enzymes such as, for example, proteases, amylases, lipases, cutinases, cellulases or peroxidases. Other ingredients include enhancers, stabilizing agents, bactericides, optical brighteners and perfumes. The enzymatic compositions may take any suitable physical form, such as a powder, an aqueous or non aqueous liquid, a paste or a gel.

Having thus described the phenol oxidizing enzymes of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of percent weight per volume (w/v). As used herein, dilutions, quantities, etc., which are expressed in terms of % (v/v), refer to percentage in terms of volume per volume. Temperatures referred to herein are given in degrees centigrade (C). The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLE 1

Purification

This example illustrates the purification of the *Stachybotrys chartarum* phenol oxidizing enzyme having the amino acid sequence as shown in FIG. 2.

*Stachybotrys chartarum* was grown on PDA plates (Difco) for about 5–10 days. A portion of the plate culture (about ¾x¾ inch) was used to inoculate 100 ml of PDB (potato dextrose broth) in 500-ml shake flask. The flask was incubated at 26–28 degrees C., 150 rpm, for 3–5 days until good growth was obtained.

The broth culture was then inoculated into 1 L of PDB in a 2.8-L shake flask. The flask was incubated at 26–28 degrees C., 150 rpm, for 2–4 days until good growth was obtained.

A 10-L fermentor containing a production medium was prepared (containing in grams/liter the following components: glucose 15; lecithin 1.51; t-aconitic acid 1.73; $KH_2PO_4$ 3; $MgSO_4.7H_2O$ 0.8; $CaCl_2.2H_2O$ 0.1; ammonium tartrate 1.2; soy peptone 5; Staley 7359; benzyl alcohol 1; tween 20 1; nitrilotriacetic acid 0.15; $MnSO_4.7H_2O$ 0.05; NaCl 0.1; $FeSO_4.7H_2O$ 0.01; $CoSO_4$ 0.01; $CaCl_2.2H_2O$ 0.01; $ZnSO_4.7H_2O$ 0.01; $CuSO_4$ 0.001; $ALK(SO_4)2.12H_2O$ 0.001; $H_3BO_3$ 0.001; $NaMoO_4.2H_2O$ 0.001). The fermentor was then inoculated with the 1-L broth culture, and fermentation was conducted at 28 degrees C. for 60 hours, under a constant air flow of 5.0 liters/minute and a constant agitation of 120 RPM. The pH was maintained at 6.0.

The cells from one liter of broth were removed from the fermentation broth by centrifugation and the supernatant was further clarified by filtering through a DE filter. The low molecular weight salts were removed by diafiltration against 4 volumes of a buffer containing 20 mM MOPS adjusted to pH 7.0 using an Amicon YM10 membrane.

An ion exchange column containing 25 mls of Poros HQ-20 resin was used to purify the enzyme. The column was first equilibrated with 5 column volumes (125 mls) of 20 mM MOPS pH 7.0. Five mls of sample containing 5–10 mgs of total protein was loaded onto the column. The column was then washed with 3 column volumes of the MOPS buffer, then eluted with a gradient of 0–0.5M ammonium sulfate in a volume of 250 mls. The flow rate was 10 mls/min. Fractions were collected in 5 mls volumes. Each fraction was assayed for phenol oxidase activity using the ABTS method. The fractions that contained ABTS activity were subjected to electrophoresis on SDS PAGE. The bands on the gel that corresponded to the ABTS activity were cut out and the amino acid sequence was determined.

The data shown below is from another purification run and shows the presence of *Stachybotrys* oxidase B band on an SDS PAGE. In this purification, crude material from the fermentation was purified on an ion exchange column using HQ20. The fractions were subjected to an initial non-denaturing (native) gel electrophoresis on a 4–20% Tris-Glycine gel. Samples were diluted with tracking dye and the running buffer was Laemmli buffer. This initial gel to look at purity was done on all fractions of the elution peak of interest and the resulting gel was silver stained. The second gel to confirm the active protein was done on every other fraction of the same peak and overlaid at pH7 and pH10 with ABTS. For the ABTS overlay, 4.5 mM ABTS was prepared at pH 7 and pH 10 (pH 7 with 50 mM sodium acetate and pH 10 with 50 mM sodium borate). The gel was divided into two parts for overlay: lanes 1–5 were overlaid with pH 7 and lanes 6–10 were overlaid with pH 10. Bands that were positive for ABTS were cut out and homogenized with Laemmli buffer and tracking dye containing BME. Samples were then placed at 100° C. for 5 minutes and loaded onto a Tris-glycine 4–20% gradient gel. The running buffer was Laemmli with 20% SDS. The gel was then silver stained.

The results of the initial denaturing gel, the ABTS overlay gel and the SDS-PAGE gels are shown in FIGS. 8, 9 and 10, respectively.

EXAMPLE 2

Amino Acid Sequence Analysis Of *Stachybotrys chartarum* Phenol Oxidizing Enzyme

*Stachybotrys chartarum* phenol oxidizing enzyme prepared as disclosed in Example 1 was subjected to SDS polyacrylamide gel electrophoresis and isolated. The isolated fraction was treated with urea and iodoacetamide and digested by the enzyme endoLysC. The fragments resulting from the endoLysC digestion were separated via HPLC (reverse phase monobore C18 column, CH3CN gradient) and collected in a multititer plate. The fractions were analysed by MALDI for mass determination and sequenced via Edman degradation. The following amino acid sequences were determined and are shown in amino terminus to carboxy terminus orientation: The following amino acid sequences were determined and are shown in amino terminus to carboxy terminus orientation:

N' FVNSGENTSPNSVHLHGSFSR C' (SEQ ID NO:5)

N' GVEPYEAAGLKDVVWLAR C' (SEQ ID NO:6)

EXAMPLE 3

Cloning Genomic Nucleic Acid

Two degenerated primers were designed based on the peptide sequences provided in Example 2. Primer 1 contains the following sequence: GTCAACAGTGGNGARAAYAC (SEQ ID NO:7) and primer 2 contains the following sequence: GCGGCCTCATANGGCTCNAC (SEQ ID NO:8) where N represents a mixture of all four nucleotides (A, T, C and G), R represents a mixture of A and G and Y represents a mixture of T and C.

For isolation of genomic DNA encoding phenol oxidizing enzyme, DNA isolated from *Stachybotrys chartarum* (MUCL #38898) was used as a template for PCR. The DNA was diluted 100 fold with Tris-EDTA buffer to a final concentration of 88 ng/ul. Ten microliter of diluted DNA was added to the reaction mixture which contained 0.2 mM of each nucleotide (A, G. C and T), 1×reaction buffer, 0.542 microgram of primer 1 and 0.62 microgram of primer 2 in a total of 100 microliter reaction in an eppendorf tube. After heating the mixture at 100° C. for 5 minutes, 2.5 units of Taq DNA polymerase was added to the reaction mix. The PCR reaction was performed at 95° C. for 1 minute, the primer was annealed to the template at 50° C. for 1 minute and extension was done at 72° C. for 1 minute. This cycle was repeated 30 times with an additional cycle of extension at 68° C. for 7 minutes. The PCR fragment detected by agarose gel contained a fragment of about 1.3 kilobase which was then cloned into the plasmid vector pCR-II (Invitrogen). The 1.3 kb insert was then subjected to nucleic acid sequencing. The sequence data revealed that it was the gene encoding *Stachybotrys chartarum* phenol oxidase B because the deduced peptide sequence matched the peptide sequences disclosed in Example 2 sequenced via Edman degradation. The PCR fragments containing the 5' gene and 3' gene were then isolated using the inverse PCR method with four primers deduced based on the sequence data from the 1.3 kb PCR fragment. FIG. 3 provides the full length genomic sequence (SEQ ID NO:3) of the *Stachybotrys* phenol oxidase B gene (spoB) including the promoter and terminator sequences.

EXAMPLE 4

Comparison Of The *Stachybotrys chartarum* Phenol Oxidizing Enzyme B With Other Oxidizing Enzymes The translated protein sequence (shown on FIG. 2) (SEQ ID NO:2) was used as query to search DNA and protein databases. It showed that *Stachybotrys* oxidase B shared 67% identity to the bilirubin oxidase at the protein sequence level. FIG. 4 shows the sequence alignment of the two proteins using the GAP program of GCG software (University Research Park, Madison, Wis.) with following parameters: Gap Weight=12; Length Weight=4; Gap Creation Penalty=8; and Gap Extension Penalty=2.

EXAMPLE 5

Expression Of *Stachybotrys* Oxidase B In *Aspergillus nicer* var. *awamori*

The DNA fragment containing nucleic acid encoding the *Stachybotrys* phenol oxidizing enzyme B flanked by two newly introduced restriction enzyme sites (BamHI and AgeI) was isolated by PCR. This PCR fragment was first cloned into the plasmid vector pCR-II and subjected to nucleic acid sequencing to verify the gene sequence (FIG. 1). This DNA fragment was then cloned into the Bgl II to Age I site of vector (pGAPT2) to create a plasmid of pGAPT2-spoB, see FIG. 5. The expression plasmid was designated as pGAPT2-spoB (FIG. 5) which is capable of integrating into the host genome. The DNA fragment containing nucleic acid encoding the *Stachybotrys* phenol oxidizing enzyme flanked by two newly introduced restriction enzyme sites (BamHI and AgeI) was also cloned into the plasmid vector pRAX1 which is identical to the plasmid pGAPT2 except a 5259 bp HindIII fragment of *Aspergillus nidulans* genomic DNA fragment AMA1 sequence (Molecular Microbiology 1996 19:565–574) was inserted. The expression plasmid designated as pRAX1-spoB (FIG. 6), which is capable of being maintained as a replicating plasmid, was then transformed into *Aspergillus* strain GCAP4 (Gene 1990, 86:153–162) by standard PEG methods. Transformants were selected on plates without uridine. Three transformants were grown on -uridine plates for 3 days. The spores from transformants were resuspended in water with 0.01% tween80. The spores (100, 1000 or 10,000) were added to the 96 well microtiter plates containing 160 ul of PROC medium. After 5 days growth at 30° C., these samples were shown to have ABTS activities. One thousand spores were added to 50 ml PROC medium in 250 ml shake flasks and after 3 days growth at 30° C., the ABST activity was 0.33 units/ml. After 4 days growth at 30° C. activity, the ABTS activity was at 4.8 units/ml. About 1.2 million of spores were also added to one liter PROC medium in 2.8 liter shake flasks. Production of *Stachybotrys* phenol oxidase B protein reached 1 unit/ml at day 3 and 4 units/ml at day 4 and activity was detected in the ABTS assay.

EXAMPLE 6

Expression Of Phenol Oxidizing Enzyme In *Trichoderma reesei*

The expression plasmid for use in transforming *Trichoderma reesei* was constructed as follows. The ends of the BamHI to AgeI fragment shown in FIG. 5 containing the gene encoding the *Stachybotrys* phenol oxidizing enzyme B were blunted by T4 DNA polymerase and inserted into Pmel restriction site of the *Trichoderma* expression vector, pTREX, a modified version of pTEX disclosed in PCT Publication No. WO 96/23928, which publication is herein incorporated by reference, which contains a CBHl promoter and terminater for gene expression and a *Trichoderma pyr*4 gene as a selection marker for transformants. The linear DNA fragment containing only the CBH1 promoter, the phenol oxidizing gene (spoB), the CBH1 terminater and selection marker pyr4 was isolated from a gel and was used to transform a uridine auxotroph strain of *Trichoderma reesei* (see U.S. Pat. No. 5,472,864) which has the four major cellulase genes deleted. Stable transformants were isolated on *Trichoderma* minimal plates without uridine. The transformants were grown on 50 ml of Proflo medium in shake flasks for 4 days at 28° C. to 30° C. and expression of the phenol oxidizing enzyme B was assayed by ABTS as described in Example 8. Proflo medium is composed of (g/l) Proflo 22.5; lactose 30.0; $(NH_4)_2SO_4$ 6.5 $KH_2PO_4$ 2.0; $MgSO_47$ $H_2O$ 0.3; $CaCL_20.2$; $CaCO_3$ 0.72; trace metal stock solution 1.0 ml/l and 10% Tween 80 2.0 ml/l. The trace metal stock solution used had (g/l) $FeSO_4.7H_2O$ 5.0; $MnSO_4.H_2O$ 1.6; $ZnSO_4.7H_2O$ 1.4; $COCl_2.6H_2O)$ 2.8.

EXAMPLE 7

Purification Of *Stachybotrys* Phenol Oxidase B

The *Stachybotrys* phenol oxidase B culture broth obtained as described in Example 5 was withdrawn from the shake flask, cooled to 4° C., and centrifuged in a Sorval centrifuge for 15 minutes at 10,500 rpm using a GSA rotor. The resulting supernatant was then removed from the pellet and concentrated 6–10 fold by ultrafiltration using a TFF holder and cartridge UF from Millipore Corporation (6 ft^2 PTGC 10K polyethersulfone Cat.#CDUF006TG). The concentrate was washed with 4 volumes of Di water by diafiltration, resulting in a recovery yield between 40–80%. The material was then centrifuged again to remove the solids, and filtered through a 0.45$\mu$ filter. The enzyme containing filtrate was then further purified using anion exchange column chromatography. In this regard, a Q-Sepharose anion exchange column was equilibrated with 50 mM potassium phosphate buffer, pH 6.9. Concentrate (enzyme mixture described above) was diluted 1 part to 4 parts (5 parts total) with 20 mM Potassium Phosphate buffer, pH 6.9 and loaded on the column at 120 mL/minute. The majority of contaminants were eluted with 20 mM Potassium Phosphate buffer, pH 6.9, containing 300 mM NaCl. Subsequently the column was eluted with the buffer containing 500 mM NaCl at a flow rate of 120 ml/minute. Respective fractions were then obtained. The respective fractions containing the highest phenol oxidizing enzyme activities were pooled together, concentrated and diafiltered to milli-Q using an Amicon concentrator with a YM10 membrane. Phenol oxidizing enzyme activity was then determined using the standard assay procedure based on the oxidation of ABTS, as described in Example 8. The enzyme activity so measured was 61.4 U/ml at pH5 and 6.1 U/mL at pH9.

EXAMPLE 8

ABTS Assay

The following example describes the ABTS assay used for the determination of phenol oxidizing activity. The ABTS assay is a spectrophotometric activity assay which uses the following reagents: assay buffer=50 mM sodium acetate, pH 5.0; 50 mM sodium phosphate, pH 7.0; 50 mM sodium carbonate, pH 9.0. The ABTS (2,2'-azinobis 3 ethylbenzothiazoline-6-sulphonic acid]) was a 4.5 mM solution in distilled water. 0.75 ml assay buffer and 0.1 ml ABTS substrate solution are combined, mixed and added to a cuvette. A cuvette containing buffer-ABTS solution was used as a blank control. 0.05 ml of enzyme sample was added, rapidly mixed and placed into the cuvette containing buffer-ABTS solution. The rate of change in absorbance at 420 nm was measured, ΔOD 420/minute, for 15 seconds (or longer for samples having activity rates<0.1) at 30° C. Enzyme samples having a high rate of activity were diluted with assay buffer to a level between 0.1 and 1.

EXAMPLE 9

Bleaching Of Tomato Stains

This example illustrates the use of the *Stachybotrys* phenol oxidizing enzyme having the sequence as shown in FIG. 2 in modifying the color associated with tomato stains.

The experiments were performed in 250 ml containers, to which 15 ml of wash solution were added (indicated in tables). The pH of the wash solution was set to pH 9. Purified phenol oxidase from *Stachybotrys* was added to the wash solution at 6 mg/l. As the enhancers phenothiazine-10-propionate (PTP) was used, dosed at 250 mM. The following formulation was used as wash solution (2 gr/liter):

| Detergent Composition: | |
|---|---|
| LAS | 24% |
| STP | 14.5% |
| Soda ash | 17.5% |
| silicate | 8.0% |
| SCMC | 0.37% |
| Blue pigment | 0.02% |
| Moisture/salts | 34.6% |

The swatches were washed for 30 minutes, at 30° C. After the wash, the swatches were tumble-dried and the reflectance spectra were measured using a Minolta spectrometer. The color differences between the swatch before and after the wash data were expressed in the CIELAB L*a*b* color space. In this color space, L* indicates lightness and a* and b* are the chromaticity coordinates. Color differences between two swatches are expressed as ΔE, which is calculated from the following equation:

$$\Delta E=\sqrt{\Delta L^2+\Delta\alpha^2+\Delta b^2}$$

The results, as ΔE values, are shown in Table 1 below:

| Wash without bleach system | Wash with bleach system |
|---|---|
| ΔE = 6.8 | ΔE = 12.2 |

As can be seen from the ΔE values, the bleaching of the tomato stain is improved in the presence of the enzyme/enhancer system.

We claim:

1. An isolated phenol oxidizing enzyme having at least 68% identity to the phenol oxidizing enzyme having the amino acid sequence as disclosed in SEQ ID NO:2.

2. The phenol oxidizing enzyme of claim 1 wherein said enzyme is obtainable from a *Stachybotrys* including *S. parvispora, S. chartarum, S. kampalensis, S. theobromae, S. bisbyi, S. cylindrospora, S. dichroa, S. oenanthes* and *S. nilagerica*.

3. The phenol oxidizing enzyme of claim 1 having the amino acid sequence as disclosed in SEQ ID NO:2.

4. An isolated polynucleotide encoding the amino acid having the sequence as shown in SEQ ID NO:2.

5. The isolated polynucleotide of claim 4 having at least 65% identity to the nucleic acid sequence disclosed in SEQ ID NO: 1 or SEQ ID NO:3.

6. The isolated polynucleotide of claim 5 having the nucleic acid sequence as disclosed in SEQ ID NO:1.

7. The isolated polynucleotide of claim 5 having the nucleic acid sequence as disclosed in SEQ ID NO:3.

8. An isolated polynucleotide capable of hybridizing to the polynucleotide having the sequence as shown in SEQ ID NO:1 or SEQ ID NO:3 under conditions of high stringency.

9. An expression vector comprising the polynucleotide of claim 4.

10. An expression vector comprising the polynucleotide of claim 5.

11. An expression vector comprising the polynucleotide of claim 8.

12. A host cell comprising the expression vector of claim 9, claim 10, or claim 11.

13. The host cell of claim 12 that is a filamentous fungus.

14. The host cell of claim 13 wherein said filamentous fungus includes *Aspergillus* species, *Trichoderma* species and *Mucor* species.

15. The host cell of claim 13 that is a yeast.

16. The host cell of claim 15 wherein said yeast includes *Saccharomyces, Pichia, Schizosaccharomyces, Hansenula, Kluyveromyces*, and *Yarrowia* species.

17. The host cell of claim 13 wherein said host is a bacterium.

18. The host cell of claim 17 wherein said bacterium includes *Bacillus* and *Escherichia* species.

19. A method for producing a phenol oxidizing enzyme in a host cell comprising the steps of:

a) culturing a host cell comprising a polynucleotide encoding said phenol oxidizing enzyme, wherein said enzyme has at least 68% identity to the amino acid sequence disclosed in SEQ ID NO:2 under conditions suitable for the production of said phenol oxidizing enzyme; and (b) optionally recovering said phenol oxidizing enzyme produced.

20. The method of claim 19 wherein said phenol oxidizing enzyme is obtainable from a *Stachybotrys* including *S. parvispora, S. chartarum, S. kampalensis, S. theobromae, S. bisbyi, S. cylindrospora, S. dichroa, S. oenanthes* and *S. nilagerica.*

21. The method of claim 19 wherein said phenol oxidizing enzyme is obtainable from *S. chartarum* and has the amino acid sequence as disclosed in SEQ ID NO:2.

22. The method of claim 19 wherein said polynucleotide comprises the sequence as shown in SEQ ID NO:1 or SEQ ID NO:3.

23. The method of claim 19 wherein said host cell includes filamentous fungus, yeast and bacteria.

24. The method of claim 23 wherein said yeast includes *Saccharomyces, Pichia, Schizosaccharomyces, Hansenula, Kluyveromyces*, and *Yarrowia* species.

25. The method of claim 23 wherein said filamentous fungus includes *Aspergillus* species, *Trichoderma* species and *Mucor* species.

26. The method of claim 25 wherein said filamentous fungus is a species of *Aspergillus.*

27. The method of claim 26 wherein the filamentous fungus is *Aspergillus niger* var. *awamori.*

28. The method of claim 23 wherein said filamentous fungus is a species of *Trichoderma.*

29. The method of claim 28 wherein said *Trichoderma* species is *Trichoderma reseei.*

30. A method for producing a host cell comprising a polynucleotide encoding a phenol oxidizing enzyme, comprising the steps of:

(a) obtaining a polynucleotide encoding a phenol oxidizing enzyme having at least 68% identity to the amino acid sequence disclosed in SEQ ID NO:2;

(b) introducing said polynucleotide into said host cell; and (c) growing said host cell under conditions suitable for the production of said phenol oxidizing enzyme.

31. The method of claim 30 wherein said host cell includes filamentous fungus, yeast and bacteria.

32. The method of claim 31 wherein said filamentous fungus includes *Aspergillus* species, *Trichoderma* species and *Mucor* species.

33. The method of claim 32 wherein said *Aspergillus* species is *Aspergillus niger* var. *awamori.*

34. The method of claim 32 wherein said *Trichoderma* species is *Trichoderma reseei.*

35. The method of claim 31 wherein said yeast is a *Saccharomyces* species.

36. The method of claim 35 wherein said *Saccharomyces* species is *Saccharomyces cerevisiae.*

37. The method of claim 30 wherein said polynucleotide has at least 65% identity to the nucleic acid shown in SEQ ID NO:1 or SEQ ID NO:3.

38. The method of claim 30 wherein said polynucleotide has the nucleic acid sequence as shown in SEQ ID NO:1 or SEQ ID NO:3.

39. The method of claim 30 wherein said polynucleotide is introduced on a replicating plasmid.

40. The method of claim 30 wherein said polynucleotide is integrated into the host cell genome.

41. An enzymatic composition comprising the phenol oxidizing enzyme of claim 1.

42. The enzymatic composition of claim 41 comprising phenol oxidizing enzyme having the sequence as shown in SEQ ID NO:2.

* * * * *